(12) United States Patent
Merlin

(10) Patent No.: US 11,040,082 B2
(45) Date of Patent: Jun. 22, 2021

(54) COMPOSITIONS AND METHODS FOR TREATING COLORECTAL CANCER

(71) Applicant: Georgia State University Research Foundation, Inc., Atlanta, GA (US)

(72) Inventor: Didier Merlin, Decatur, GA (US)

(73) Assignees: Georgia State University Research Foundation, Inc., Atlanta, GA (US); The United States Government as Represented by The Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/502,060

(22) PCT Filed: Aug. 6, 2015

(86) PCT No.: PCT/US2015/044046
§ 371 (c)(1),
(2) Date: Feb. 6, 2017

(87) PCT Pub. No.: WO2016/022821
PCT Pub. Date: Feb. 11, 2016

(65) Prior Publication Data
US 2017/0224759 A1  Aug. 10, 2017

Related U.S. Application Data

(60) Provisional application No. 62/033,874, filed on Aug. 6, 2014.

(51) Int. Cl.
| | |
|---|---|
| *A61K 38/00* | (2006.01) |
| *A61P 35/00* | (2006.01) |
| *A61K 38/06* | (2006.01) |
| *C07K 5/00* | (2006.01) |
| *A61K 45/06* | (2006.01) |
| *A61K 38/05* | (2006.01) |
| *G01N 33/574* | (2006.01) |
| *C07K 5/068* | (2006.01) |
| *C07K 5/09* | (2006.01) |
| *C07K 5/062* | (2006.01) |
| *C07K 5/078* | (2006.01) |
| *A61K 31/197* | (2006.01) |
| *A61K 31/655* | (2006.01) |
| *A61P 1/04* | (2006.01) |
| *A61K 39/395* | (2006.01) |

(52) U.S. Cl.
CPC ............ *A61K 38/06* (2013.01); *A61K 31/197* (2013.01); *A61K 31/655* (2013.01); *A61K 38/05* (2013.01); *A61K 39/395* (2013.01); *A61K 45/06* (2013.01); *A61P 1/04* (2018.01); *A61P 35/00* (2018.01); *C07K 5/06026* (2013.01); *C07K 5/06052* (2013.01); *C07K 5/06086* (2013.01); *C07K 5/06165* (2013.01); *C07K 5/0815* (2013.01); *G01N 33/57419* (2013.01); *G01N 2800/50* (2013.01)

(58) Field of Classification Search
None
See application file for complete search history.

(56) References Cited

U.S. PATENT DOCUMENTS

2003/0108523 A1* 6/2003 Lipton .................. A61K 38/34
424/93.2

FOREIGN PATENT DOCUMENTS

EP          1621553          2/2006

OTHER PUBLICATIONS

Ahmadi et al., World J. Gastroenterol. 15:61-66 (2009) (Year: 2009).*
Shah et al., Rev. Gastroenterol. Disord. 3:S3-S10 (2007) (Year: 2007).*
Anderson et al., J. Pharm. Exp. Ther. 332:220-228 (2010) (Year: 2010).*
Ingersoll et al., Am. J. Physiol. Gastrointest. Liver Physiol. 302:G484-G492 (2012) (Year: 2012).*
Grivennikov et al., Gastroenterology 150:808-810 (2016) (Year: 2016).*
Dalmasso et al., "PepT1-Mediated Tripeptide KPV Uptake Reduces Intestinal Inflammation," *Gastroenterology*, 134(1):166-178, 2008.
Thwaites et al., "H-coupled Nutrient, Micronutrient and Drug Transporters in the Mammalian Small Intestine," *Exp. Physiol.*, 92(4):603-619, 2007.

* cited by examiner

*Primary Examiner* — Thea D'Ambrosio
(74) *Attorney, Agent, or Firm* — Pabst Patent Group LLP

(57) ABSTRACT

The present invention relates to methods of treating a patient who has colorectal cancer and to methods of reducing the likelihood that a patient will develop or experience a recurrence of colorectal cancer. The methods comprise a step of introducing, to the patient, an effective amount of an agent that targets an intestinal $H^+$-coupled di/tripeptide transporter (PepT1). Useful compositions including, for example, the tripeptide KPV, vectors encoding such peptides, and cells (e.g., bacterial cells) including them, are also within the scope of the present invention, as are kits including such compositions.

12 Claims, 9 Drawing Sheets
Specification includes a Sequence Listing.

SEQUENCE LISTING

<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: Synthetic Primer

<400> SEQUENCE: 1
acaagtcgga ggcttaatta cacat                                          25

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
ttgccattgc acaactcttt tc                                              22

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
cactctcaag ggcggtcaaa                                                 20

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
tacgatccag gcttcccggg t                                               21

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
gtcaaccgca cctttatgct                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gttgagcacc tgcttcatca                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
ggttgccaag ccttatcgga                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
cttctcaccc agggaattca    20

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer

<400> SEQUENCE: 9
aggctgcccc gactacgt    18

<210> SEQ ID NO 10
<211> LENGTH: 27
<212> TYPE: DNA
<213> ORGANISM: Artificial Sequence
<220> FEATURE:
<223> OTHER INFORMATION: Synthetic Primer

<400> SEQUENCE: 10
gactttctcc tggtatgaga tagcaaa    27

<210> SEQ ID NO 11
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 11
tccaggcttt gggcatca    18

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
ctttatcagc tgcacatcac tcaga    25

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide Dimer
<220> FEATURE:
<221> NAME/KEY: CC
<222> LOCATION: (4)..(5)
<223> OTHER INFORMATION: a Cys-Cys linker between two units of KPV, (CKPV)2

<400> SEQUENCE: 13

Val Pro Lys Cys Cys Lys Pro Val
1               5

COMPOSITIONS AND METHODS FOR TREATING COLORECTAL CANCER

CROSS REFERENCE TO RELATED APPLICATIONS

This application is a U.S. national phase application filed under 35 U.S.C. § 371 of International Application No. PCT/US15/44046, filed on Aug. 6, 2015, which claims the benefit of the filing date of U.S. Provisional Application No. 62/033,874, which was filed Aug. 6, 2014. The entire content of these prior applications is hereby incorporated by reference herein.

STATEMENT REGARDING FEDERALLY FUNDED RESEARCH

This invention was made with government support under grant number RO1-DK-071594 awarded by the National Institutes of Health and grant number BX-002526 awarded by the Department of Veterans Affairs. The government has certain rights in the invention.

REFERENCE TO SEQUENCE LISTING

The Sequence Listing submitted Jan. 27, 2020, as a text file named "GSURF_2013-25_ST25.txt," created on Jan. 6, 2020, and having a size of 2,934 bytes is hereby incorporated by reference pursuant to 37 C.F.R. § 1.52(e)(5).

FIELD OF THE INVENTION

The present invention relates to compositions and methods for treating colon cancer and more particularly to methods that utilize therapeutic agents that target PepT1, a proton-coupled transporter for di- and tripeptides expressed by intestinal epithelial cells.

BACKGROUND OF THE INVENTION

The proton-coupled oligopeptide transporter (POT) family includes four transporter proteins belonging to the SLC15A solute carrier group (Daniel and Kottra, *Pflugers Archiv:European Journal of Physiology* 447:610-8, 2004). One POT member, PepT1, is a di- and tri-peptide transporter that is primarily expressed in the small intestine in healthy individuals. PepT1 is understood to transport di- and tri-peptides, but not single amino acids or peptides with more than three amino acids, from the intestinal lumen into epithelial cells via an inwardly directed proton gradient (Ingersoll et al., *Am. J. Physiol. Gastrointest. Liver Physiol.* 302:G484-92, 2012). Under normal physiological conditions, intestinal epithelial cells apically express PepT1, which aids in the transport and absorption of di- and tripeptides from endogenous sources into the intestinal cells. There is some controversy regarding whether PepT1 is also expressed in colonic tissues. Multiple studies have reported little or no PepT1 expression at mRNA levels in the colons of healthy humans and rodents (Drozdzik et al., *Mol. Pharmaceutics* 11:3547-3555, 2014; Englund et al., *Eur. J. Pharm. Sci.* 29:269-277, 2006; Jappar et al. *Drug Metabolism and Disposition* 38:1740-1746, 2010; Meier et al., *Drug Metabolism and Disposition* 35:590-594, 2007; Merlin et al., *Gastroenterol.* 120:1666-1679, 2001; Ogihara et al., *Biochem. Biophys. Res. Comm.* 220:848-852, 1996; Ziegler et al., *Am J. Clin. Nutr.* 75:922-930, 2002; Ma et al., *Pharmaceutical Res.* 29:535-545, 2012). Other reports have suggested that the PepT1 mRNA is regionally distributed in the colon, with little or no expression in the proximal colon and an increased expression in the distal colon (Jappar et al. *Drug Metabolism and Disposition* 38:1740-1746, 2010; Meier et al., *Drug Metabolism and Disposition* 35:590-594, 2007; Wuensch et al., *Am. J. Physiol., GI and Liver Physiol.* 305:G66-73, 2013). One previous study used immunofluorescence to show that PepT1 protein is expressed in the proximal colon at a steady state, but the potential transport functions of colonic PepT1 were not investigated (Wuensch et al., supra).

During chronic inflammation, the expression profile of PepT1 within the gastrointestinal (GI) tract is altered. In patients with chronic diseases such as inflammatory bowel disease (IBD) and short bowel syndrome, PepT1 expression is upregulated in the colon (Merlin et al., *Gastroenterology* 120:1666-79, 2001; Ziegler et al., *Am. J. Clin. Nutr.* 75: 922-30, 2002). In an animal model, colonic PepT1 is highly expressed in IL10−/− mice with colitis but not in *Lactobacillus plantarum* treated IL10−/− mice lacking any sign of colitis (Chen et al., *Am. J. Physiol. Gastrointest. Liver Physiol.* 299:G1287-97, 2010). It has also been shown that colonic PepT1 expression/function may be induced in mice under pathological conditions of the colon, such as in the event of *Citrobacter rodentium* infection (Nguyen et al., *Gastroenterology* 137:1435-47 e1-2, 2009). In addition to di- and tri-peptides from the diet and other endogenous sources, PepT1 has also been shown to transport di- and tri-peptides from bacteria, including N-formyl-methionine-leucine-phenylalanine (fMLP; Merlin et al., *J. Clin. Invest.* 102:2011-8, 1998; Charrier et al., *Lab Invest.* 86:490-503, 2006), muramyl dipeptide (MDP; Vavricka et al., *Gastroenterology* 127:1401-9, 2004) and L-Ala-gamma-D-Glu-mDAP (Tri-DAP; Dalmasso et al., *Am. J. Physiol. Gastrointest. Liver Physiol.* 299:G687-96, 2010). Since the small intestine is the primary site of PepT1 expression, and PepT1 is expressed minimally or not at all in the healthy colon, there is normally limited interaction between bacterial peptides and PepT1. However, previous in vitro results from our laboratory and others have demonstrated that bacterial peptide-PepT1 interactions in colonic epithelial cells can trigger downstream pro-inflammatory events, including increased production of inflammatory cytokines via activation of the NF-κB pathway and deregulation of colonic miRNA expression (Vavricka et al., *Gastroenterology* 127:1401-9, 2004; Dalmasso et al., *Am. J. Physiol. Gastrointest. Liver Physiol.* 299:G687-96, 2010; Ayyadurai et al., *PLoS One* 9:e87614, 2014; and Buyse, *Am. J. Physiol. Cell Physiol.* 283:C1795-800, 2002). These findings suggest that PepT1 could play a crucial role in cell-to-cell communication during colitis. In the context of IBD in humans, a functional hPepT1 SNP (rs2297322) was recently linked to the presence of IBD in Swedish patients free of the NOD2 mutation (Zucchelli et al., *Inflamm. Bowel Dis.* 141:1334-1345, 2011), suggesting that this mutation may contribute to the pathology of IBD. However, additional studies are needed to explore how this mutation affects the expression and function of PepT1 during IBD.

In previous studies (Shi et. al., *Dig. Dis. Sci.* 51:2087-93, 2006), we designed transgenic (TG) mice that overexpressed PepT1 under the control of the villin promoter (which confers specific expression in intestinal epithelial cells) and obtained PepT1-KO mice from Deltagene (San Mateo, Calif.), in order to examine how PepT1 overexpression and deletion, respectively, affect intestinal inflammation using various model of colitis models. Our results demonstrated that overexpression of PepT1 in intestinal epithelial cells leads to increased inflammation and exacerbated colitis pathology (Dalmasso et al., *Gastroenterology* 141:1334-45, 2011). In TG mice treated with 4,4'-diaminodiphenylsulfone (DDS), the degree of pathology was correlated with increased pro-inflammatory cytokine production, increased neutrophil infiltration and greater weight loss compared to wild-type (WT) mice. Importantly, DSS-treated PepT1-KO mice developed a moderate colitis compared to WT mice (Ayyadurai et al. *Lab. Invest.*, 93:888-99, 2013). Histological examination revealed that DSS-treated PepT1-KO mice produced fewer pro-inflammatory cytokines, had reduced neutrophil infiltration, and lost less weight compared to DSS-treated WT mice. In addition, knockout of PepT1 decreased the chemotaxis of immune cells recruited to the intestine during inflammation. Finally, phenotypes observed with both TG and PepT1-KO mice were linked to the presence of the gut microbiota since they were attenuated by antibiotic treatment (Dalmasso et. al., *Gastroenterology* 141: 1334-45, 2011). Together, we believe these findings suggest that PepT1 expression in immune cells can regulate the secretion of pro-inflammatory cytokines triggered by bacteria and/or bacterial products, and thus may play a role in the induction of colitis.

SUMMARY

In a first aspect, the present invention features methods of treating a patient who has colorectal cancer or reducing the likelihood that a patient will develop or experience a recurrence of colorectal cancer. The methods comprise a step of administering to the patient an effective amount of an agent that targets an intestinal $H^+$-coupled di/tripeptide transporter (PepT1).

In a second aspect, the invention features pharmaceutical compositions comprising therapeutically effective amounts of a first agent that targets an intestinal $H^+$-coupled di/tripeptide transporter (PepT1) and a second agent that treats inflammatory bowel disease or colorectal cancer. The first agent and the second agent can be included in the composition as distinct entities or they can be joined (e.g., fused or conjugated) to one another. In case of any doubt, where a composition includes a first agent and a second agent, at least two distinct agents are present.

In a third aspect, the invention features kits including the pharmaceutical compositions described herein and instructions for use.

In the methods of the present invention and where the present compositions are used in the preparation of a medicament (e.g., in the preparation of a medicament for treating colorectal cancer or an inflammatory bowel disease), an "effective amount" of the agent to be administered to a patient who has been diagnosed with colorectal cancer is an amount whose administration is positively correlated with a decrease in tumor number, tumor size, tumor burden, colonic inflammation, colonic cellular infiltration, colonic epithelial proliferation, or colonic aberrant crypt foci; an "effective amount" of the agent to be administered to a patient who is considered to be at risk (e.g., an elevated risk relative to the risk faced by a cohort of patients) of colorectal cancer is an amount that delays the onset or reduces the severity of colorectal cancer (by, for example, reducing tumor number, size or burden); and an "effective amount" of the agent to be administered to a patient who has been diagnosed with an inflammatory bowel disease is an amount whose administration is positively correlated with reduced colonic inflammation. Unless the context indicates otherwise, we may use the terms "effective amount", "therapeutically effective amount", and "therapeutic amount" interchangeably. We tend to use the latter two terms where a patient has been diagnosed with colorectal cancer and/or IBD.

In describing the invention, we may include lists of various agents and other moieties. It is to be generally understood that, unless the context clearly indicates otherwise, any combination of the listed agents can be used in the present invention, and any one or more of the listed agents or other moieties can be specifically excluded from a given composition or method.

In describing the invention, we have referred to methods of treatment, and it is to be understood that the features of that aspect of the invention can be expressed, alternatively, as a "use" of the compositions described herein. For example, as aspect of the invention is the use of a composition described herein in the preparation of a medicament for treating colon cancer.

BRIEF DESCRIPTION OF THE DRAWINGS

FIG. 1A is a series of photographs of representative colon samples obtained from each experimental group (as labeled therein) at the end of the AOM/DSS protocol. FIG. 1B is a bar graph showing the number of tumors per mouse. In FIG. 1C, tumor size was determined using a dissecting microscope fitted with an ocular micrometer. The tumor size distribution is graphed. In FIG. 1D, the tumor areas for each colon were summed and are presented as the tumor burden index. FIG. 1E is representative images of H&E-stained colonic sections from WT or TG mice treated with AOM/DSS or given unmodified water (control). In FIG. 1F, the colonic mRNA levels of IL-6, Cxcl-2, IL-22, IL-10 and Tnf-α were quantified by qRT-PCR and normalized to mRNA levels of the ribosomal protein, 36B4. Symbols: scale bar, 100 µm; *=$p<0.05$; =$p<0.01$; and *=$p<0.001$.

In FIG. 2A, we reproduce photomicrographs showing the levels of epithelial cell proliferation in colonic tissue sections from WT and TG mice treated with AOM/DSS or water alone. The tissues were assessed by immunohistochemistry using the proliferation marker, Ki67. FIG. 2B is a bar graph representing the number of Ki67$^+$ cells, which were counted and averaged per crypt. FIG. 2C is a panel of photomicrographs in which apoptotic colonic epithelial cells were quantified in the type of each animal shown using a TUNEL assay (FITC, green in the original) and nuclei were stained with DAPI (blue in the original). FIG. 2D is a bar graph in which cells positive for both TUNEL and DAPI staining were counted and averaged per crypt. FIG. 2E is a collection of photomicrographs in which the levels of β-catenin were assessed by immunohistochemical analysis of colonic tissue sections from WT and TG mice treated with AOM/DSS or water alone. The scale bars in the 20× images represent 50 µm, while those in the 60× images represent 20 µm. FIG. 2F is a photograph of a Western blot showing the protein levels of phosphorylated IκκB-αβ, phosphorylated IκB-α, β-catenin, phosphorylated-ERK1/2 and total ERK1/2 in the colons of WT or TG mice treated with AOM/DSS or water alone. FIG. 2G is a bar graph representing densitometric quantifications of a Western blot normalized to β-actin. Symbols: scale bar, 50 μm; *, $p<0.05$; ***, $p<0.001$.

FIG. 3A is a series of photographs of representative colons obtained from each experimental group at the end of the AOM/DSS protocol. FIG. 3B is a bar graph illustrating the number of tumors per mouse. FIG. 3C is also a bar graph illustrating the outcome of tumor size as determined using a dissecting microscope fitted with an ocular micrometer. The tumor size distribution is graphed. FIG. 3D is also a bar graph illustrating the tumor areas summed for each colon; the data is presented as the tumor burden index. FIG. 3E is a line graph comparing AOM/DSS-treated WT mice and PepT1-KO mice weighed on day 0, daily during each DSS treatment, and once per week during each 2-week post-DSS recovery period. The graph represents the % values of the original day 0 weights. FIG. 3F shows representative images of H&E-stained colonic sections from WT or PepT1-KO mice treated with AOM/DSS or water alone. FIG. 3G is a bar graph showing the colonic mRNA levels of IL-6, CXCL-2, IL-22, IL-10 and TNF-α quantified by qRT-PCR and normalized to mRNA levels of the ribosomal protein, 36B4. Symbols: scale bar=50 μm; *, $p<0.05$; and **, $p<0.01$.

FIG. 4A is a series of photomicrographs showing the levels of epithelial cell proliferation in colonic tissue sections from WT and PepT1-KO mice treated with AOM/DSS or water alone. The tissue was assessed by immunohistochemistry using the proliferation marker, Ki67. FIG. 4B is a bar graph illustrating the number of Ki67$^+$ cells, which were counted and averaged per crypt. FIG. 4C is a series of photomicrographs of apoptotic colonic epithelial cells quantified using a TUNEL assay (FITC, green in the original), and nuclei were stained with DAPI (blue in the original). FIG. 4D is a bar graph illustrating the cells positive for both TUNEL and DAPI, which were counted and averaged per crypt. FIG. 4E is a photograph of a Western blot. The protein levels of phosphorylated IκκB-αβ, phosphorylated and total IκB-α, β-catenin, phosphorylated-ERK1/2 and total ERK1/2 in the colons of WT or PepT1-KO mice treated with AOM/DSS or water alone were analyzed. FIG. 4F is a bar graph representing densitometric quantifications of Western blot data normalized to β-actin. Symbols: scale bar, 50 μm; *=$p<0.05$; =$P<0.01$; and *=$p<0.001$.

FIG. 5A is a bar graph showing the results of quantitating the colonic mRNA levels of PepT1 by qRT-PCR and normalizing the results to mRNA levels of the ribosomal protein, 36B4. FIG. 5B is a photomicrograph of an immunohistochemical analysis of mouse PepT1 that was performed on colonic tissue sections from wild-type (WT) mice treated with AOM (10 mg/kg body weight) plus two cycles of 2.5% DSS, or water alone. Microscopic images were taken at 20× magnification. FIG. 5C is a photograph of a Western blot of whole-colon lysates that were used to analyze mouse PepT1 expression. β-Actin was detected as the loading control. Symbols: =$p<0.01$ and *=$p<0.001$.

FIG. 6A is a series of photomicrographs in which human PepT1 antibody was used to observe PepT1 levels in a human tissue microarray counterstained with hematoxylin. The tissue microarray included samples from normal patients, patients with benign colon tumors, and colon cancer patients with various stages of colon adenocarcinoma. FIG. 6B is a bar graph obtained by scoring the anti-human PepT1-stained slides according two parameters: the intensity of the staining and the area of positive cells in the epithelium. Concerning intensity, the tissue was assigned a score of 0 when PepT1 positive cells were absent, a score of 1 when there was low intensity staining, and a score of 2 when there was high intensity staining. Regarding area, the tissue was assigned a score of 0 in the absence of PepT1 positive cells, a score of 1 when less than the half of the epithelium was PepT1 positive, and a score of 2 when half or more of the epithelium was PepT1 positive. The intensity was indexed by the surface parameter giving one final score for each slide. Symbols: Scale bar: 100 μm; *=$p<0.05$.

FIG. 7A is a series of photographs of representative colons obtained from each experimental group at the end of the AOM/DSS protocol. FIG. 7B is a bar graph illustrating the number of tumors per mouse. FIG. 7C is a bar graph illustrating tumor size, which was determined using a dissecting microscope fitted with an ocular micrometer. The tumor size distribution is graphed. FIG. 7D is also a bar graph showing the sum of the tumor areas of each colon, presented as the tumor burden index. FIG. 7E is a line graph charting the animals' weights. Mice were weighed on day 0, daily during the two DSS treatments, and once per week during the 2-week recovery period that followed each DSS or DSS/KPV treatment. The graph represents the % values of the original day 0 weight. FIG. 7F shows representative images of H&E-stained colonic sections from both experimental groups. FIG. 7G shows epithelial cell proliferation in colonic tissue sections from each experimental group as assessed by immunohistochemistry using the proliferation marker, Ki67. Scale bar=50 μm. FIG. 7H is a bar graph; Ki67$^+$ cells were counted and averaged per crypt. Symbols: Scale bar=50 μm; *=$p<0.05$; =$p<0.01$; and *=$p<0.001$.

FIG. 8A is a series of photographs of representative colons obtained from each experimental group at the end of the AOM/DSS protocol. FIG. 8A is a bar graph showing the number of tumors per mouse. FIG. 8C is a bar graph showing tumor size, as determined using a dissecting microscope fitted with an ocular micrometer. The tumor size distribution is graphed. FIG. 8D is also a bar graph in which the tumor areas of each colon were summed, and they are presented as the tumor burden index. FIG. 8E is a line graph tracking the animals' weights. Mice were weighed on day 0, daily during the two DSS treatments, and once per week during the 2-week recovery period that followed each DSS or DSS/KPV treatment. The graph represents the % values of the original day 0 weight.

DETAILED DESCRIPTION

Figure 1:
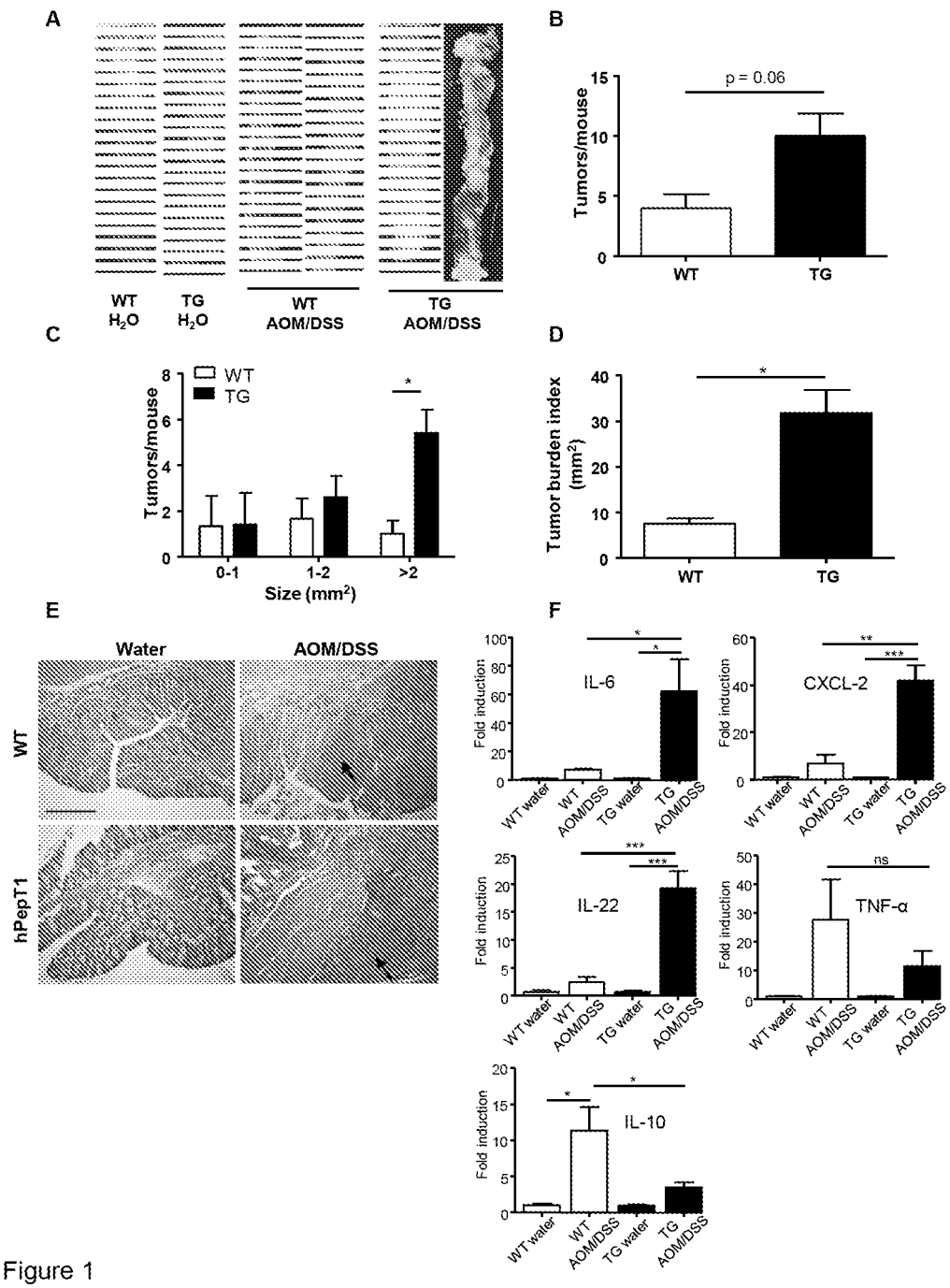
FIGS. 1A-1F are a collection of data illustrating that inflammation and tumor growth is increased in mice that overexpress PepT1 in their intestinal epithelial cells. WT and TG mice were intraperitoneally (IP) injected with azoxymethane (AOM; 10 mg/kg body weight), maintained for 7 days, and then subjected to a two-cycle DSS treatment (each cycle consisted of 7 days of exposure to 2.5% DSS in drinking water and 14 days of exposure to untreated $H_2O$).

In a first aspect, the present invention features the use of the compositions described herein in methods of treating a patient who has colorectal cancer or in methods of reducing the likelihood that a patient will develop or experience a recurrence of colorectal cancer. The cancer may be present as either a primary occurrence or due to metastasis from another site, and it may or may not be associated with inflammation in the colon (e.g., it may not have been preceded by an inflammatory bowel disease). The methods of treating the patient can include a step of administering to the patient an effective amount of an agent that targets an intestinal $H^+$-coupled di/tripeptide transporter (PepT1). By "targets," we mean that the agent interacts with PepT1 or the nucleic acid encoding it and, in some embodiments, inhibits the expression or activity of PepT1. For example, when a peptide, such as KPV, is transported into a cell via PepT1, the peptide has interacted with PepT1 and therefore targets PepT1. The interaction may be, but is not necessarily, selective; an agent that targets PepT1 may interact with other moieties, including other transporters on the same cell or a different cell. Where an agent targets PepT1 by inhibiting the expression or activity of PepT1, the targeting is more likely to be selective. For example, where the activity of PepT1 is inhibited by an antibody or other such binding agent, the antibody or binding agent is likely to selectively target PepT1 by interacting with it to the exclusion of other moieties. Similarly, where a nucleic acid is used to inhibit the expression of PepT1, it is likely that the nucleic acid will be sequence-specific to the extent that it will selectively hybridize with PepT1-encoding mRNA to the exclusion of other RNAs.

Agents Targeting PepT1: Given that the compositions and methods of the invention can include a plurality of agents, we may refer to an agent that targets PepT1 as a "first" agent. Various formulations are contemplated, as described further below. For example, the first agent or compositions including the first agent (e.g., pharmaceutical or physiologically acceptable compositions) can be formulated for oral administration or parenteral administration (e.g., intravenous, intramuscular, intraperitoneal, subcutaneous, transmucosal, or transdermal administration).

In any particular embodiment of the invention (whether in the context of a method or composition), the first agent can be a di- or tri-peptide, for example, the tri-peptide Lys-Pro-Val (KPV), the tri-peptide fMLP, or the di-peptide Lys-Pro, Pro-Val, Val-Ala, or Gly-Sar. KPV is derived from α-melanocyte stimulating hormone (α-MSH). It has been shown to have anti-inflammatory properties (Luger et al., *Ann. NY Acad. Sci.* 994:133-140, 2003; Brzoska, et al., *Endocr. Rev.* 29:581-602, 2008) and to effectively reduce colitis in chemically-induced mice (Dalmasso et al., *Gastroenterology* 134:166-78, 2008; Laroui et al., *Gastroenterology* 138:843-853, e1-2, 2010; Kannengiesser et al., *Inflamm. Bowel Dis.* 14:324-331, 2008). Therefore, we also hypothesized that KPV may attenuate tumorigenesis during the AOM/DSS-induced model of colon cancer. Overall, we found that increased PepT1 expression in the intestine led to increased colonic tumor burden in TG mice. However, we also found that PepT1 made a plausible therapeutic target, as KPV treatment decreased the number of tumors and cellular proliferation in colonic epithelial cells.

In some embodiments, the peptide therapeutics described herein can be administered as multimers (e.g., dimers and trimers). The peptide therapeutic can also be the Cys-linked dimer $(CKPV)_2$ (SEQ ID NO:13) as disclosed, e.g., in Gatti et al., *J Surg. Res.* 131:209-214, 2006). The amino acids within the peptides can be variously present in the D- or L-form. For example, the tri-peptide can be L-Lys-L-Pro-L-Val (KPV) or the synthetic stereochemical analog (L-Lys-L-Pro-D-Val; KP-D-V) (see, e.g., Elliott et al., *J Invest. Dermatol.* 122:1010-1019, 2004). The amino acid residues within the peptides may be naturally occurring, or the peptides may include non-naturally occurring residues. The amino acid residues may also be modified post-translationally at one or more of their side chains or at either or both of the C- or N-termini. The posttranslational modification can include the introduction of a phosphate, acetate, amide group, or methyl group, and the peptides may also be glycosylated or lipidated. Post-translational modifications can be variously introduced by expressing the peptides in different expression systems (e.g., those based on mammalian, bacterial, insect, or plant cells). Accordingly, the peptides of the invention can be produced by recombinant methods well known in the art or synthesized by chemical techniques.

In some embodiments, the first agent is a β-lactam antibiotic (e.g., a penicillin, carbapenem, cephalosporin or monobactam), an ACE-inhibitor, an ester prodrug of enalapril or fosinopril, bestatin, alafosfalin, amino acid-conjugated antiviral drugs (valacyclovir), or L-DOPA.

In some embodiments, the first agent can also be a substance without obvious peptide-like bonds, such as δ-amino-levulonic acid or an ω-amino fatty acid.

As noted, we have perceived a positive effect on colon cancer by inhibiting PepT1. Accordingly, in some embodiments, the agent that targets PepT1 is an agent that inhibits the expression or activity of PepT1. Methods of making and administering inhibitory nucleic acids and downregulating the activity of a protein, particularly a protein expressed on the cell surface, are now routine in the art. The sequence of PepT1 is known in the art, and that sequence can be readily used to design nucleic acids that mediate RNAi (e.g., siRNAs, shRNAs, antisense oligonucleotides, and microRNAs). The sequence of PepT1 can also be used to generate anti-PepT1 antibodies, and such an antibody or a fragment thereof, such as Fv fragment, $F(ab)_2$, $F(ab)_2$, and Fab and the like, can be used in the compositions and methods of the invention. Anti-PepT1 antibodies are also commercially available.

Small molecules or compounds that inhibit PepT1 include sulfonylurea antidiabetic drugs, such as nateglinide, glibenclamide, tolbutamide, chlorpropamide, sartans. Other inhibitors include ACE inhibitors and ester prodrugs thereof. In certain embodiments, the second agent is diphenoxylate, an antibiotic, sulfasalazine, a corticosteroid, or any combination thereof.

There is evidence that the agents described herein, including KPV, interact with PepT1. However, in the event that interaction is later called into question, the agents described herein can nevertheless be utilized in the present compositions and methods.

In connection with any of the methods of treatment, one can carry out a step of identifying a patient in need of treatment for colorectal cancer or a patient having an increased risk of developing colorectal cancer or experiencing a relapse. For instance, the method can include providing a biological sample (e.g., a tissue or fecal sample) from the patient and determining whether the level of PepT1 is elevated in the sample (an elevated level indicating that the patient is a good candidate for treatment or prophylactic treatment). A patient in need of treatment may also be identified using routine screening methods for colorectal cancer, such as high-sensitivity fecal occult blood test (FOBT), sigmoidoscopy, colonoscopy (optical and/or virtual), or by analyzing nucleic acids, such as DNA in, for example, blood or stool cells for genetic changes that may be a sign of colorectal cancer. We may use the terms "colorectal cancer" and "colon cancer" interchangeably, and it is to be understood that the methods of the invention can be applied to patients diagnosed as having a tumor or malignancy in the tissue of the colon or rectum of any grade or stage and regardless of the precise characteristics of that tumor or malignancy (e.g., regardless of whether the cancer is an adenocarcinoma).

When the patient to be treated has colorectal cancer, additional forms of treatment may be included in the present methods (e.g., radiation treatment, surgical intervention, or administration of a second chemotherapeutic agent). For instance, the methods of the present invention may further include administering, together or separately, a chemotherapeutic agent to the patient that is distinct from the first agent (i.e., distinct from an agent that targets PepT1). We may refer to the chemotherapeutic agent as a "second" agent. The second agent can be a chemical compound (e.g., a small molecule therapeutic), such as 5-fluorouracil (5-FU), capecitabine (Xeloda®), irinotecan (Camptosar®), oxaliplatin (Eloxatin®), leucovorin, ziv-aflibercept (Zaltrap®) or a combinations of these compounds (e.g., FOLFOX (5-FU, leucovorin, and oxaliplatin), FOLFIRI (5-FU, leucovorin, and irinotecan), FOLFOXIRI (leucovorin, 5-FU, oxaliplatin, and irinotecan), CapeOx (capecitabine and oxaliplatin), and a combination of 5-FU and leucovorin). The second agent can also be a biotherapeutic (e.g., an antibody or an engineered or recombinant protein). Examples include, but are not limited to, bevacizumab (Avastin®), cetuximab (Erbitux®), panitumumab (Vectibix®), and regorafenib (Stivarga®).

As discussed further below, the invention encompasses compositions that include a first agent as described herein and a second agent, and these agents can be included as distinct entities (e.g., as a mixture) or as a joint entity (e.g., as a fusion protein or chemical conjugate). Where the first and second agents are employed as distinct entities, they can be combined in a single formulation and administered together (i.e., at the same time and by the same route of administration) or they can be included in separate formulations that are administered simultaneously or sequentially by the same or different routes of administration. Where the first and second agents are joined, they may be fused (e.g., via a peptide or other covalent bond) or they may be non-covalently coupled.

Delivery Vehicles: As discussed further below, the first and second agents can also be attached, separately or together, to a delivery vehicle. In some embodiments, the delivery vehicles include (a) at least one nanoparticle (NP) and preferably a plurality of NPs, (b) a targeting agent that binds (e.g., specifically binds) a targeted tissue or cell, and (c) a hydrogel. We may use the terms "vehicle" and "construct" interchangeably. The vehicle is assembled such that the targeting agent is associated with the nanoparticle, thereby forming a core structure, and the hydrogel is generally peripheral to the core; the hydrogel fully or substantially encapsulates the core structures. While there may be areas of integration and overlap between a given core structure and the hydrogel, and while there may be some areas in which the hydrogel does not completely encapsulate each and every core structure, the hydrogel is generally positioned peripheral to the core structures. The targeting agent can be directly associated with the nanoparticle by covalent or non-covalent bonds or it may be indirectly associated with the nanoparticle by way of a linker.

In the vehicles, the nanoparticles can have a varied diameter, preferably in the range of about 1-1,000 nm, and such NPs can be formed by crystalline iron atoms or micelles of small molecules. The NPs within a given vehicle may be essentially or roughly of the same size, or they may vary in size. NPs of about 10-1000 nm are typically generated from polymeric materials, and any such NPs are useful in the context of the vehicles. The NPs can include more than one type of polymer and can include co-polymers. One of ordinary skill in the art will recognize that the resulting size depends on the synthetic process used to prepare the NPs, and such methods are known in the art. For example, NPs useful in the vehicles can be formed by applying energy to fragment the bulk materials or by the nucleation and growth of seeds through chemical processes. Although there is variability in the size of the NPs that can be used, in general, the NPs should be considerably smaller than the size of the cells with which they will interact (i.e., of a target cell). Nonphagocytic eukaryotic cells can internalize particles less than about 1 μm in size. NPs having a diameter of about 5-110 nm are understood to be in development as potential carriers of anticancer drugs via intracellular drug delivery.

The NPs can have an electrostatic surface charge. Zeta potential approximates the charge on a NP and is used to describe cell-nanomaterial (NM) interactions. Higher zeta (positive or negative) can produce a stronger electrostatic repulsion between NMs, and NM suspension will likely be more stable as a result. Charge depends on the polymer used for the NM matrix or can be modulated by adsorbing specific molecules onto the NM surface.

The NPs used herein can be (and generally are) spherical. The NPs used herein can be micelles, liposomes or lipid NPs, many of which have been well characterized. The NPs can have a surface area-to-volume ratio of 3/r. As r decreases, the surface area-to-volume ratio increases. A particle with a larger surface area has more interaction sites available and the rate of an interaction at the surface may be higher. Useful liposomes can be synthesized with a mixture of lipids with different surface charges (cationic, neutral, and anionic). More specifically, NPs within the vehicles can be cationic liposomes such as DOTAP, DOTMA (lipofectin) and DOSPA (lipofectamine). Any of the incorporated NPs can include polyethylene glycol, as described by Gomes-da-Silva et al.

The vehicles can include NPs formed (exclusively or partially) from naturally occurring polymers (e.g., a protein or polysaccharide).

The materials of the vehicles, including the NPs therein, can be biodegradable or non-biodegradable. Suitable biodegradable polymers include polyorthoesters, polyanhydrides, polyamides, polyalkylcyanoacrylates, polyesters, lactides and/or glycolides, polycaprolactones, polyphosphazenes, and pseudo-polyamino acids. Suitable non-biodegradable polymers include silicone, an elastomer, polyethylene oxide, polyethylene glycol, or an acrylic polymer. Suitable aliphatic polyesters include poly(D,L-lactide) and poly(glycolide) and co-polymers thereof. The polymer can be water-insoluble; the polymer can be ethyl cellulose; the polymer can be amylase/amylopectin; and polymers can be bonded via noncovalent or covalent interactions directly during the NP synthesis or after synthesis by surface modification reactions. Amide, ester, disulfide, hydrazone, or thioether linkages have been used to enable covalent or hydrophobic interactions (hydrophobic drug loading) or ionic interactions (nucleic acids) and are useful in forming the vehicles. Hydrophobic, electrostatic, or hydrogen-bonding interactions alternatives to covalent linkages, particularly if flexibility under chemical conditions is required.

In some embodiments, the vehicles employ maleimide/thiol group-mediated covalent bonding. For example, NPs (e.g., comprising PLA-PEG) can be grafted to a targeting moiety (e.g., an antibody) via maleimide/thiol group-mediated covalent bonding.

The NPs can be particulate dispersions or solid particles in which a therapeutic moiety (or "drug") and/or a diagnostic or imaging agent can be dissolved, entrapped, or attached.

The targeting agent that binds (e.g., specifically binds) a target tissue (e.g., a human cell or tissue) can be an antibody or a fragment or other variant thereof that binds the target tissue (e.g., an scFv). Although the invention is not so limited, when a TNF receptor is targeted, the antibody moiety can be adalimumab, certolizumab pegol, golimumab, or infliximab, an scFv comprising the variable regions of the heavy and light chains of adalimumab, certolizumab pegol, golimumab, or infliximab, or a biologically active variant of these tetrameric or single chain antibodies. With respect to antibody targeting agents, the targeting agent can be a tetrameric antibody, a biologically active variant thereof, an scFv, Fab fragment, Fab' fragment, or F(ab')2 fragment, or a biologically active variant thereof, regardless of class (i.e., whether of the IgG class or another class) and whether human, humanized, chimeric, polyclonal, monoclonal, or having any other attribute or characteristic described herein).

The targeting agent can also be a ligand or a peptide ligand mimetic. If desired, any combination of such agents can also be employed. A goal of active targeting is to facilitate nanoparticle accumulation in close proximity to a target cell or tissue and to permit active crossing of the cell membrane by therapeutic materials. Thus, the targeting agent incorporated in the vehicles can be a macrophage-specific ligand or receptor. More generally, the targeting agent can be a receptor, a receptor ligand, a chemoattractant agent, an extracellular matrix protein, or an antibody or biologically active variant or other fragment thereof that specifically binds a target tissue or cell affected by a bowel disease or gastrointestinal cancer.

In any of the vehicles, the targeting agent can include a protein or peptide (both amino acid polymers; the term "protein" being generally applied for longer polymers and/or "full-length" naturally occurring proteins and the term "peptide" or "polypeptide generally being applied to describe shorter polymers or fragments of full-length, naturally occurring proteins). The targeting agent can bind a cell or tissue within the gastrointestinal tract, and that cell or tissue may be cancerous.

Where the targeting agent is a receptor, it can be an integrin (e.g., integrin β2) or an active fragment or other variant thereof. Generally, biologically active fragments and other variants of naturally occurring targeting agents are useful in the vehicles so long as they retain the ability to bind (e.g., specifically bind) a target cell or tissue of interest (e.g., a macrophage or colon cancer cell). The targeting agent (e.g., an antibody) can also target (e.g., specifically bind) an extracellular matrix protein or integrin.

A variety of hydrogels can be used to encapsulate or surround (fully or partially) the core components of the vehicles. For example, one can employ a hydrogel including alginic acid and/or chitosan. For example, a NP described herein, decorated to constitute a core structure, can be encapsulated in an alginate-chitosan hydrogel as described by Laroui et al., (*Gastroenterol.* 138:843-853 e841-842, 2010). See also Laroui et al., *Nature Protocol Exchange* doi:10.1038/nprot.2009.165.

When the patient is afflicted with inflammatory bowel disease (IBD) or ulcerative colitis, the method can further include administering a second agent, together with or separately from the first agent, that treats IBD (e.g., an anti-inflammatory drug (e.g., sulfasalazine), an anti-diarrheal (e.g., diphenoxylate), an immune supressor (e.g., infliximab), an antibiotic (e.g., ciproflaxin), a steroid (e.g., predisone), and the like.). The first and second agents can be administered separately or together, in the manner discussed above in the context of treating colorectal cancer. In some embodiments, the methods explicitly exclude the aminopeptidase inhibitor bestatin from use in the invention.

The methods of treatment also encompass administering a greater number of agents. For example, the methods can include administering a plurality of agents that target PepT1 (e.g., one, two, or three di- or tripeptides that target PepT1). The methods can also include administering a plurality of agents that have distinct chemotherapeutic or anti-inflammatory properties together with a PepT1-targeting agent. In yet another embodiment, the method can include administering a plurality (e.g. 2-4, inclusive) of agents that target PepT1 and a plurality of distinct chemotherapeutic and/or anti-inflammatory agents (e.g., 2-4 chemotherapeutic agents and/or 2-4 anti-inflammatory agents). The pharmaceutical compositions of the method can be formulated accordingly.

Thus, another aspect of the present invention relates to pharmaceutical compositions that include a therapeutically effective amount of a first agent that targets an intestinal $H^+$-coupled di/tripeptide transporter (PepT1) and a second agent, distinct from the first, that treats colorectal cancer or an inflammatory bowel disease (e.g., colitis).

Gene therapies and modulation of the microbiome: While oral formulations of the agents described herein have certain advantages, including convenience to the patient, the agents of the invention can be formulated and delivered by gene therapies or by modulating the microbiome such that it delivers an agent (e.g., a peptide) to the region of the cancer. For example, a nucleic acid construct encoding a first and/or second agent can be incorporated into a vector (e.g., a plasmid, a viral vector, or a bacterium) according to methods well known in the art and administered to the patent. In other embodiments, the agent(s) can be delivered by way of an alteration to the gut microbiome; bacteria expressing the agent(s) are formulated according to methods known in the art and delivered to the patient.

The compositions of the present invention can be formulated to be administered by methods commonly known in the art. In certain embodiments, the compositions of the present invention are formulated for oral administration (e.g., in the form of capsules, tablets, powders, granules, or as a suspension or liquid). In other embodiments, the compositions are formulated for parenteral administration (e.g., intravenous, intramuscular, intraperitoneal, subcutaneous, transmucosal, or transdermal administration).

The compositions of the invention may contain other ingredients, such as conventional non-toxic, pharmaceutically-acceptable carriers, penetration enhancers, adjuvants or vehicles. The ingredients must be pharmaceutically acceptable and efficacious for their intended administration, and cannot degrade the activity of the active ingredients in the composition to any level below which they would no longer be effective. In some cases, the pH of the formulation may be adjusted with pharmaceutically acceptable acids, bases or buffers to enhance the stability of the formulated compound or its delivery form.

The formulations may also be provided in the form of nanoparticles to enhance delivery and targeting of the active ingredients. (See, for example, Cho et al., *Clin. Cancer Res.* 14:1310-1316,2008).

For oral administration, the formulation may contain binders, such as crystalline cellulose, cellulose derivatives, acacia, corn starch, or gelatins. Additionally, the formulation may be presented with disintegrators, such as corn starch, potato starch, or sodium carboxymethylcellulose. The formulation may be further presented with dibasic calcium phosphate anhydrous or sodium starch glycolate. Additionally, the formulation may be presented with lubricants, such as talc or magnesium stearate.

For parenteral administration, the formulation may be prepared by dissolving the agents in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation also may be delivered by any mode of injection.

For transdermal administration, the formulation may contain with skin penetration enhancers, such as propylene glycol, polyethylene glycol, isopropanol, ethanol, oleic acid, N-methylpyrrolidone, and the like, which increase the permeability of the skin to the active agent, and permit agent to penetrate through the skin and into the bloodstream. The composition may be combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch.

Yet another aspect of the present invention relates to pharmaceutical compositions comprising an effective amount of a first agent that targets an intestinal $H^+$-coupled di/tripeptide transporter (PepT1) and second agent, distinct from the first, that treats inflammation or colorectal cancer. In certain embodiments, the second agent administered, either together with or separately from the first, is a chemical compound (e.g., a small molecule) or a biotherapeutic (e.g., a peptide, an antibody or an antigen-binding fragment or variant thereof).

Kits: Another aspect of the present invention relates to kits comprising a first agent that targets an intestinal $H^+$-coupled di/tripeptide transporter (PepT1), a second agent, distinct from the first agent, that is useful in treating IBD or colorectal cancer, and instructions for use. Additional ingredients and items can also be included. For example, the kits can include a composition including a first and/or a second agent in a concentrated or lyophilized form and a diluent for resuspension. Other items can be paraphernalia used to deliver the compositions. For example, the kits can include one or more syringes, needles, tubing, sterile gauze, material for wound dressing, a tourniquet, gloves (e.g., latex gloves), or any combination of these elements. The kit is used to administer an effective amount of a first agent that targets an intestinal $H^+$-coupled di/tripeptide transporter (PepT1), and/or an effective amount of a second agent, distinct from the first, that treats IBD or colorectal cancer.

Patients amenable to treatment: The invention features methods of treating a patient who has colorectal cancer, as well as methods of reducing the likelihood that a patient will develop or experience a recurrence of colorectal cancer. Colorectal cancer (CRC) is one of the most common malignancies (Weir et al., *J. Natl. Cancer Inst.* 95:1276-99, 2003) and the known link between chronic intestinal inflammation and CRC development has given rise to the term "colitis-associated cancer" (CAC; Merlin et al., *Gastroenterology* 120:1666-79, 2001; Wojtal et al., *Drug Metabolism and Disposition: the Biological Fate of Chemicals* 37:1871-1877, 2009). Patients amenable to treatment with the present methods may have been diagnosed as having either CRC or, if they also suffer from colitis, CAC. Development of CAC in patients suffering from ulcerative colitis (UC) is one of the best clinically characterized examples of an association between intestinal inflammation and carcinogenesis (Eaden et al., *Gut* 48:526-535, 2001; Ullman and Itzkowitz, *Gastroenterology* 140:1807-1816, 2011). For instance, in UC patients, the risk for colon cancer increases from 2% 10 years after initial diagnosis to 8% after 20 years and to 18% after 30 years (Eaden et al., *Gut* 48:526-535, 2001). In contrast, the lifetime risk of sporadic colorectal cancer in the United States is 5% (Thorsteinsdottir et al., *Nat. Rev. Gastroenterol. Hepatol.* 8:395-404, 2011).

Previous studies suggest PepT1 may be an ideal target for the transport of drugs that promote an anti-inflammatory environment in the colon during chronic inflammation, as it is only upregulated in the colon during chronic disease. In addition to transporting various metabolic di- and tripeptides, PepT1 also has the ability to transport many types of drugs/prodrugs (Adibi, *Am. J. Physiol. Gastrointest. Liver Physiol.* 285:G779-788, 2003; Thwaites and Anderson, *Exp. Physiol.* 92:603-619, 2007; Newstead, *Biochem. Soc. Trans.* 39:1353-1358, 2011), including the anti-inflammatory tripeptide, KPV (Dalmasso et al., *Gastroenterology* 134:166-78, 2008). In some embodiments, the present methods can be carried out with patients who have colon cancer that is not associated with inflammation of the colon.

We expect at least the peptide agents described herein to be effective over a broad range of concentrations, including picomolar concentrations that normally occur in human plasma. Accordingly, the compositions and methods of the invention include those in which the therapeutic agent(s) are formulated and/or delivered in a manner to achieve circulating plasma concentrations in the picomolar range (e.g., about 1-1000 µM).

Where formulated for oral administration, the active agent or agents administered can be incorporated into a pill, tablet, capsule, or the like. For example, the agent(s) can be formulated as a hard gelatinous tablet that includes gelatin bloom 30 (~70.0 mg), maltodextrin MD 05 (~108.0 mg), di-α-tocopherol (~2.0 mg), sodium ascorbate (~10.0 mg) a cellulose (e.g., microcrystalline cellulose) (~48.0 mg), magnesium stearate (~2.0 mg), and the active agent(s) at $0.2 \times 10^{-9}$-$0.2 \times 10^{-13}$ mg. When formulated as a hard tablet, the composition can include, for example anhydrous lactose (~130.5 mg), a cellulose (e.g., microcrystalline cellulose) (~80.0 mg) di-α-tocopherol (~2.0 mg), sodium ascorbate (~10.0 mg), polyvinylpyrrolidone K30 (~5.0 mg), magnesium stearate (~2.0 mg), and the active agent(s) at ~$0.2 \times$ $10^{-9}$-$0.2\times10^{-13}$ mg. ("~" signifies "about" and, by "about," in relation to any aspect of the invention, we mean a value that includes an inherent variation of error for the device or the method being employed to determine the value or plus-or-minus 10% of the value, whichever is greater.)

EXAMPLES

In the present study, we hypothesized that PepT1 is involved in CAC development due to its role in intestinal inflammation. To test this hypothesis, we used both TG or PepT1-KO mice and employed a well-known murine model of CAC using the carcinogen, azoxymethane (AOM), followed by two cycles of DSS (Chen J et al., *Cancer Biol. Ther.* 8:1313-7, 2009; De Robertis et al., *J. Carcinog* 10:9, 2011).

The human intestinal $H^+$-coupled di/tripeptide transporter, hPepT1, is expressed primarily in the small intestine and minimally or not at all in the colon. hPepT1 colonic expression is upregulated in patients who have a chronic disease, such as inflammatory bowel disease (IBD), although its exact role in pathogenesis is unclear. We have previously shown that the overexpression of hPepT1 in the colon exacerbates colitis in mice, and previous human studies have demonstrated that chronic intestinal inflammation in the colon can result in the development of colorectal cancer.

In the study described below, we demonstrated that, compared to wild type (WT) animals, colonic tumor burden was increased in AOM/DSS-treated TG mice that overexpress PepT1 in intestinal epithelial cells and decreased in AOM/DSS-treated PepT1-KO mice. The specific upregulation of PepT1 in the colon during chronic disease and especially colon cancer, as shown in this study using a human colon-microarray stained for PepT1, suggests that it may be an ideal target for transporting drugs with anti-inflammatory properties.

PepT1 has been shown to transport many types of drugs/ prodrugs (Adibi et al., *Am. J. Physiol Gastrointest Liver Physiol.* 285:G779-88, 2003; Thwaites et al., *Exp. Physiol.* 92:603-19, 2007; Newstead et al., *Biochem. Soc. Trans.* 39:1353-8, 2011), including KPV (Dalmasso et al., *Gastroenterology* 134:166-78,2008), an anti-inflammatory tripeptide which is derived from α-melanocyte stimulating hormone (α-MSH) (Luger et al., *Ann. N. Y. Acad. Sci.* 994:133-40, 2003; Brzoska et al., *Endocr. Rev.* 29:581-602, 2008) and to effectively reduce chemically-induced colitis in mice (Dalmasso et al., *Gastroenterology* 134:166-78,2008; Laroui et al., *Gastroenterology* 138:843-53 el-2, 2010; Kannengiesser et al., Inflamm. Bowel Dis. 14:324-31, 2008). Therefore, we hypothesized that KPV may attenuate tumorigenesis in the AOM/DSS-induced murine model of colon cancer.

We indeed observed that KPV was able to decrease both the number of tumors and the proliferation of malignant colonic epithelial cells in a PepT1-dependent way. This confirms our hypothesis that PepT1 can be a therapeutic target for the treatment of colon cancer and indicates that targeting PepT1 can reduce the risk of recurrent tumorigenesis. The following materials and methods were used in this study.

Mice: Eight-week old female TG mice, PepT1-KO mice, and the respective WT strains (background matching C57BL/6 mice and FVB/NJ mice) were used in this study. Mice were housed in specific pathogen-free conditions and fed ad libitum. All the experiments involving mice were approved by institutional animal care and use committee (IACUC, Georgia State University Atlanta, Ga., USA, permit number A11027, A11025 and A11023).

Colonic tumor model: Colon cancer was induced as previously described with some modifications (Greten et al., *Cell* 118:285-96, 2004). Mice were intraperitoneally injected with AOM (Sigma-Aldrich, St. Louis, Mo.) diluted in PBS (10 mg/kg) and maintained on a regular diet and water for 5 days. The mice were then subjected to two cycles of DSS treatment (MP Biomedicals, Solon, Ohio, USA), with each cycle consisting of 2.5% DSS for 7 days followed by a 14-day recovery period with regular water. Mice were then sacrificed and their colons isolated for further experimentation. Colonic tumors were counted and measured using a dissecting microscope. The total sum of the area of each colon covered by tumor tissue was expressed as the tumor burden index.

In experiments designed to test the efficacy of KPV (Biopeptide Co. Inc., San Diego, Calif.), the above protocol was slightly modified. Five days after AOM injections (10 mg/kg to WT mice or 15 mg/kg to PepT1-KO mice), the WT and PepT1-KO mice were given 3% DSS with or without KPV for seven days. Following the 7-day treatment, the mice were given normal drinking water for 14 days, then 2.5% DSS (WT) or 3% DSS (PepT1-KO mice) with or without KPV for seven days. Following the 7-day treatment, the mice were given normal drinking water for 14 days. The KPV-treated group received 100 μM KPV in their drinking water along with the DSS during both DSS cycles. While receiving DSS treatment, mice were weighed daily to ensure they did not lose greater than 20% of their original body weight.

Human Colon Tissue Microarray: Human colon tissue array slides were purchased from US Biomax, Inc. (Rockville, Md.). The microarray slide consisted of 75 samples in duplicate of normal, reactive and cancerous (of different grades and stages) colon tissue. The previously described antibody against hPepT1 (Merlin et al., *Gastroenterology* 120:1666-1679, 2001) was used to stain the array slides at US Biomax, Inc. and subsequent imaging were performed by employees of US Biomax, Inc. and then sent to our laboratory. The images were then analyzed for epithelial hPepT1 staining (Rabbit h-PepT1, dilution 1:3000). Images were scored according to two parameters (from 0 to 2): the intensity of the staining (0: absence of PepT1 positive cells, 1: low intensity staining, 2: High intensity staining) and the area of positive cells in the epithelium (0: absence of PepT1 positive cell, 1: less than the half of the epithelium is PepT1 positive, 2: the half or more of the epithelium is PepT1 positive). The intensity was indexed by the surface parameter giving one final score for each slide.

H&E Staining of Colonic Tissue: Mouse colons were fixed in 10%-buffered formalin for 24 hours at room temperature and then embedded in paraffin. Tissues were sectioned at 5-μm thickness and stained with hematoxylin & eosin (H&E) using standard protocols. Images were acquired using an Olympus microscope equipped with a DP-23 digital camera.

Immunohistochemistry: Mouse colonic tissues were fixed in formalin and paraffin-embedded. For Ki67, β-catenin and PepT1 staining, sections were deparaffinized. Slides were incubated in sodium citrate buffer (pH 6.0) and cooked in a pressure cooker for 10 minutes for antigen retrieval. Sections were then blocked with 5% goat serum in TBS followed by incubation for one hour with anti-Ki67 (1:100, Vector Laboratories, Burlingame, Calif.), anti-β-catenin (1:1000, Cell Signaling, Danvers, Mass.) or anti-mPepT1 at 37° C. After washing with TBS, sections were treated with appropriate biotinylated secondary antibodies for 30 minutes at 37° C., and color development was performed using the Vectastain ABC kit (Vector Laboratories). Sections were then counterstained with hematoxylin, dehydrated, and then coverslipped. Images were acquired using an Olympus microscope equipped with DP-23 Digital camera. Ki67-positive cells were counted per crypt.

Terminal deoxynucleotidyl transferase deoxyuridine triphosphate nick-end labeling (TUNEL) staining: To quantitate the number of apoptotic cells in colonic epithelial cells, paraffin sections were deparaffinized and stained for apoptotic nuclei according to the manufacturer's instructions using the In Situ Cell Death Detection Kit (Roche Diagnostics, Indianapolis, Ind.). Images were acquired using an Olympus microscope equipped with a Hamamatsu black and white ORCA-03G digital camera. TUNEL-positive cells that overlapped with DAPI nuclear staining were counted per crypt.

Cytokine expression levels: Total RNAs were extracted from colonic tissues using RNeasy mini Kit (Qiagen, Valencia, Calif.) according to the manufacturer's instructions. Yield and the quality of RNAs were verified with a Synergy 2 plate reader (BioTek, Winooski, Vt., USA). cDNAs were generated from the total RNA isolated above using the Maxima first-strand cDNA synthesis kit (Thermo Scientific, Lafayette, Colo., USA). mRNA expressions were quantified by quantitative real-time reverse transcription-PCR (qRT-PCR) using Maxima SYBR green/ROX (6-carboxyl-X-rhodamine) quantitative PCR (qPCR) Master Mix (Thermo Scientific) and the following sense and antisense primers:

```
IL-6:
                                    (SEQ ID NO: 1)
5'-ACAAGTCGGAGGCTTAATTACACAT-3'
and (SEQ ID NO: 2)
5'-TTGCCATTGCACAACTCTTTTC-3';

CXCL2:
                                    (SEQ ID NO: 3)
5'-CACTCTCAAGGGCGGTCAAA-3'
and (SEQ ID NO: 4)
5'-TACGATCCAGGCTTCCCGGGT-3';

IL-22:
                                    (SEQ ID NO: 5)
5'-GTCAACCGCACCTTTATGCT-3'
and (SEQ ID NO: 6)
5'-GTTGAGCACCTGCTTCATCA-3';

IL-10:
                                    (SEQ ID NO: 7)
5'-GGTTGCCAAGCCTTATCGGA-3'
and (SEQ ID NO: 8)
5'-CTTCTCACCCAGGGAATTCA-3';

tumor necrosis factor α (TNF α)
                                    (SEQ ID NO: 9)
5'-AGGCTGCCCCGACTACGT-3'
and
```

```
                                    (SEQ ID NO: 10)
5'-GACTTTCTCCTGGTATGAGATAGCAAA-3';

36B4
                                    (SEQ ID NO: 11)
5'-TCCAGGCTTTGGGCATCA-3'
and (SEQ ID NO: 12)
5'-CTTTATCAGCTGCACATCACTCAGA-3'.
```

Results were normalized by using 36B4 housekeeping gene.

Western blot: Whole colon lysates were made by homogenizing a small piece of distal colon in Radio-Immunoprecipitation Assay (RIPA) buffer plus Halt phosphatase and protease inhibitor cocktail (Thermo Fisher Scientific Inc.). 50 µg of lysate per well were resolved on polyacrylamide gradient gels and transferred to nitrocellulose membranes (Bio-Rad, Hercules, Calif.). Membranes were probed with relevant primary antibodies, including β-catenin, p-Iκκ-α/β, β-actin (Cell Signaling), mPepT-1, p-ERK1/2, and total ERK1/2 (Santa Cruz Biotechnology, Inc., Santa Cruz, Calif.), followed by incubation with appropriate HRP-conjugated secondary antibodies (GE Healthcare Biosciences, Pittsburgh, Pa.). Blots were developed using ECL Western Blotting Detection reagents (GE Healthcare Biosciences). Densitometry quantifications were performed using the software Quantity One (Bio-Rad).

Statistical Analysis: Data are presented as means±SEM. Statistical analysis for significance was determined using ANOVA test followed by a Bonferroni post-test (GraphPad Prism). Differences were noted as significant: $*P<0.05$, $P<0.01$ and $*P<0.001$.

Figure 9:
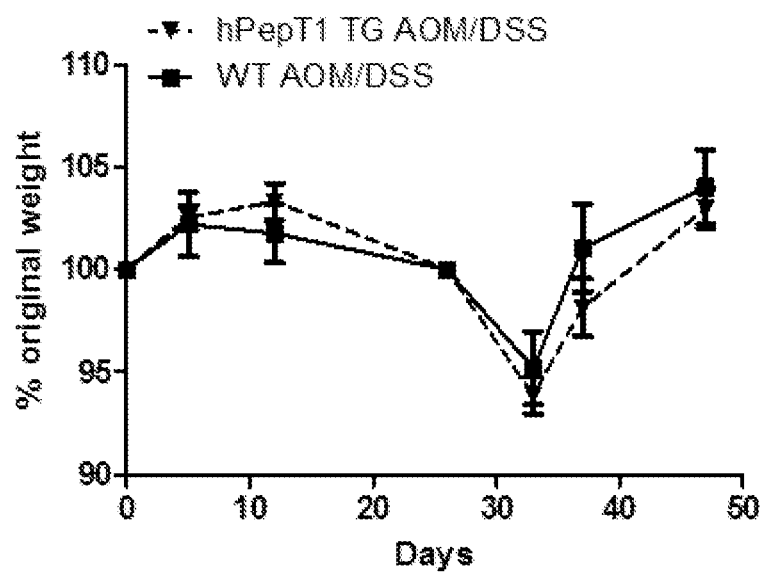
FIG. 9 is a line graph showing animals' weights. AOM/DSS-treated WT and TG mice were weighed on day 0, daily during each DSS treatment, and once per week during the 2-week recovery period after each DSS treatment. The graph represents the % values of the original day 0 weights.

Tumor growth is increased in mice that overexpress PepT1 in intestinal epithelial cells: We first examined if PepT1 overexpression in the colon could contribute to the development of CAC. Our laboratory previously generated TG mice that overexpress PepT1 under the control of the villin promoter (Dalmasso et al., *Gastroenterology* 141: 1334-45, 2011), which is primarily active in intestinal epithelial cells. When these mice were treated with AOM and two seven day cycles of DSS, they developed an increased number of tumors compared to WT mice (p=0.06) (FIG. 1A-1B). The number of large tumors (>2 mm$^2$) was highly increased in TG versus WT mice (FIG. 1C), as was the overall tumor burden index (i.e., the total area of tumors per colon) (FIG. 1D), demonstrating that TG mice are more susceptible to tumorigenesis, with an enhanced tumor growth and/or tumor cell survival. Even if we did not observe any difference in body weight loss between WT and TG mice during the AOM/DSS protocol (FIG. 9), histological examination revealed the presence of larger adenomas and increased areas of inflammatory cell infiltration in colonic sections from AOM/DSS-treated TG and WT mice (FIG. 1E), with increased dysplasia, aberrant crypt foci and cellular infiltration in the colonic epithelia of AOM/DSS-treated TG mice compared to WT mice. Histologically, we did not observe any difference between water-treated (control) TG and WT mice. Next, we determined the mRNA expression levels of pro-inflammatory cytokines and chemokines, and we importantly found that the levels of IL-6, Cxcl2 and IL-22 were significantly higher in AOM/DSS-treated TG mice compared to treated WT mice (FIG. 1F), supporting the previous observation that TG mice are more sensitive to intestinal inflammation/tumorigenesis induced by AOM/DSS treatment. The mRNA encoding TNF-α, a pro-inflammatory cytokine reported to have an increased expression in colitis and CAC (Viennois et al., *Lab. Invest.* 94:950-65, 2014), did not significantly differ between TG and WT mice (FIG. 1F). The anti-inflammatory cytokine IL-10 was expressed at lower levels in AOM/DSS-treated TG mice compared to similarly treated WT mice (FIG. 1F). In control (water-treated) TG and WT mice, we did not observe any significant difference of these cytokine levels (FIG. 1F). Taken together, these data indicate that TG mice are more susceptible to AOM/DSS treatment than WT mice, suggesting that PepT1 play a role in the initiation/exacerbation of cancer development.

Figure 2:
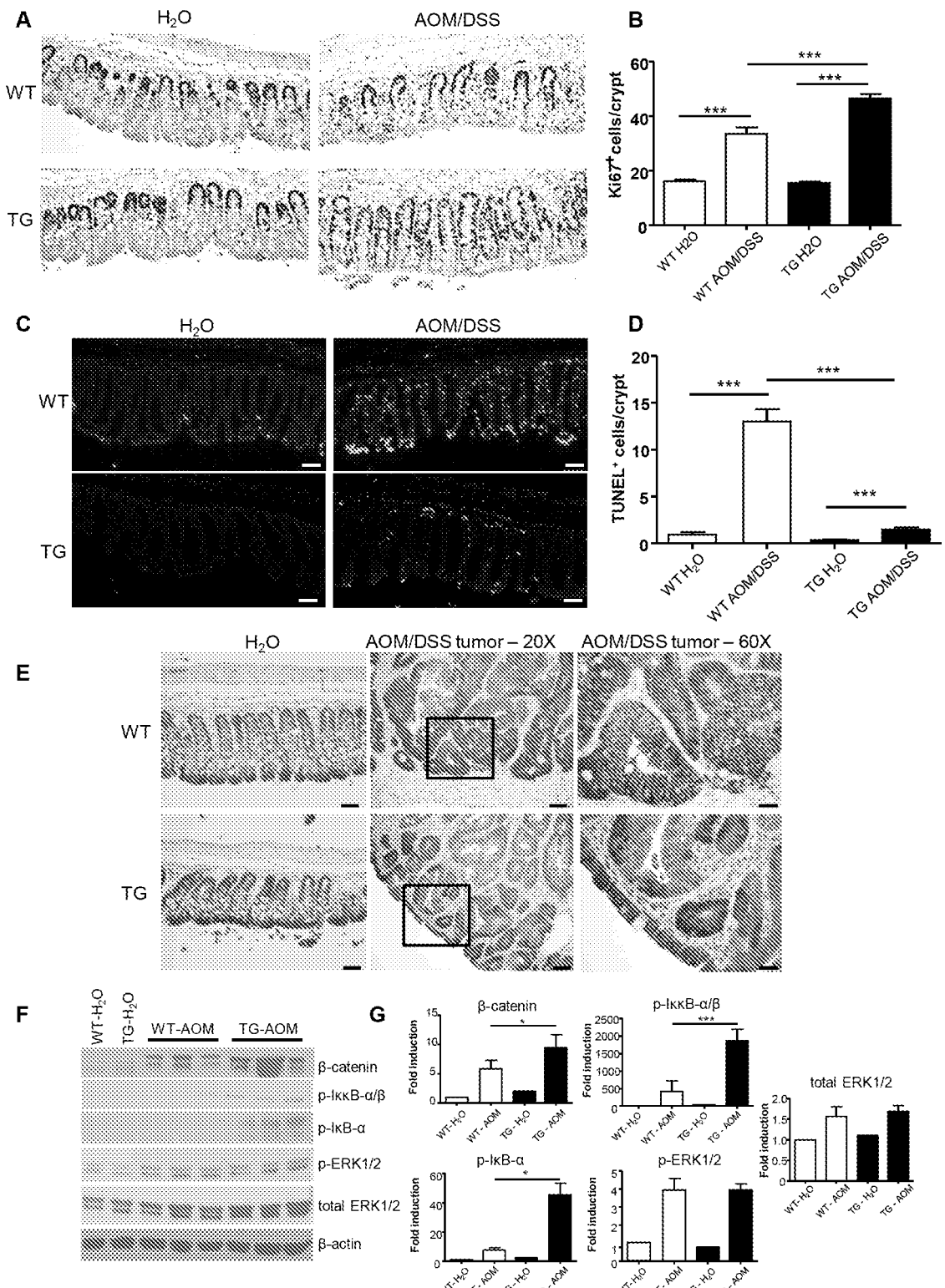
FIGS. 2A-2G are a collection of data illustrating that overexpression of hPepT1 increases colonic epithelial proliferation, decreases epithelial apoptosis and alters tumorigenesis signaling pathways.

Overexpression of hPepT1 deregulates epithelial proliferation and apoptosis: The increased tumor burden and average tumor size in TG mice suggested that they may be subject to increased cell proliferation compared to WT mice. The assessment of nuclear proliferation in the colonic epithelium was analyzed using an antibody against the marker Ki67. No significant differences in cellular proliferation between water-treated WT and TG were observed (FIGS. 2A-2B). However, following AOM and DSS treatment, the number of Ki67 positive cells was increased in both WT and TG mice but to a significantly higher level in TG mice compared to WT mice (FIGS. 2A-2B). This indicates that overexpression of hPepT1 in intestinal epithelial cells exacerbates the AOM/DSS-induced proliferation of crypt cells in the colonic epithelium. Ki67-positive cells were highly prevalent in colon tumors from both WT and TG mice. In addition, a TUNEL-based quantification of apoptosis in colonic sections from WT and TG mice revealed that the epithelia of AOM/DSS-treated WT mice had significantly more TUNEL+ cells compared to treated TG mice (FIGS. 2C-2D). AOM/DSS treatment increased the number of apoptotic cells in both WT and TG mice, but the fold change was significantly higher in the former (FIG. 2D), indicating that hPepT1 overexpression in epithelial cells minimized AOM/DSS-induced apoptosis in the colonic epithelia. Together, these data demonstrate that hPepT1 overexpression in intestinal epithelia may induce various pathways that lead to increased proliferation and/or decreased apoptosis of colonic epithelial cells, thereby potentially contributing to the increased tumor burden observed in TG mice.

Overexpression of hPepT1 alters tumorgenesis signaling pathways: Several signaling pathways have been associated with regulating tumorigenesis in the AOM/DSS CAC model and human CAC. Among them, β-catenin is an oncogenic protein that plays an important role in cell adhesion and is a co-transcriptional activator of genes in the Wnt signaling pathway including c-myc, cyclooxygenase-2, metalloproteinase-7 and cyclinD1 (Wong and Pignatelli, *Am. J. Pathol.* 160:389-401, 2002). AOM induces β-catenin mutations on specific serine and threonine residues which are targets for GSK-3β phosphorylation, leading to the cellular accumulation of β-catenin (Chen and Huang, *Cancer Biol. Ther.* 8:1313-1317, 2009). Therefore, we determined if there were differences in β-catenin levels in TG mice compared to WT mice that had been treated with AOM/DSS. β-catenin immunohistochemical staining demonstrated that free β-catenin was increased in the cytoplasm of tumor cells from AOM/DSS-treated WT and TG mice compared to the cells from water-treated (control) animals, where the majority of β-catenin staining was associated with the cellular membranes (FIG. 2E). We also observed an increased nuclear accumulation of β-catenin in tumor cells from TG mice compared to WT mice (FIG. 2E), suggesting that the transcription of β-catenin may be enhanced in these cells. Consistent with these results, AOM/DSS-treated WT and TG mice had increased levels of β-catenin compared to their water-treated counterparts, and β-catenin expression was slightly higher in colon lysates from TG mice compared to WT mice as shown after densitometric analysis of Western Blot (FIG. 2F-G). The NF-κB and MAPK pathways have also been implicated in colon tumorigenesis (Chen and Huang, *Cancer Biol. Ther.* 8:1313-1317, 2009; DiDonato et al., *Immunol. Rev.* 246:379-400, 2012). Therefore, we next examined these pathways by Western blot signaling partners. We observed highly increased levels of phosphorylated IκK-α/β and phosphorylated IκB-α in AOM/DDS-treated TG mice and only slightly increased levels in comparably treated WT mice (FIGS. 2F-2G), suggesting that NF-κB signaling is enhanced in in AOM/DDS-treated TG mice compared to WT mice. Finally, we observed increased levels of phosphorylated ERK1/2 in AOM/DSS-treated WT and TG mice compared to their respective water controls (FIGS. 2F-2G). However, the levels were not significantly different between the two treated groups, suggesting that this pathway is not required for the increased tumor growth observed in PepT1 TG mice.

Decreased tumorigenesis in PepT1-deficient mice: Next, we investigated whether the absence of PepT1 could protect the animals from the AOM/DSS-induced CAC phenotype. Following AOM/DSS-treatment, PepT1-KO mice developed significantly fewer tumors (of all sizes) compared to similarly treated WT mice (FIGS. 3A-3C). Consistent with these data, the overall tumor burden was significantly lower in AOM/DSS-treated PepT1-KO mice compared to AOM/DSS-treated WT mice (FIG. 3D). These data suggest that, in absence of PepT1, mice are protected from tumor initiation and growth. Since intestinal inflammation is known to be a central factor in the initiation and development of colon tumors, we next measured various parameters of inflammation after the induction of CAC in WT and PepT1-KO mice. Monitoring of body weight showed that WT mice underwent a dramatic weight loss during the first cycle of DSS, whereas no such effect was observed in PepT1-KO mice (FIG. 3E). Histological examinations revealed large adenomas with major lymphocyte infiltrations in colonic sections from AOM/DSS-treated WT mice (FIG. 3F), whereas no lymphocyte infiltration or adenoma was detected in AOM/DSS-treated PepT1-KO mice (FIG. 3F). We did not observe any difference in these parameters between control (water-treated) PepT1-KO and WT mice (FIG. 3F). Next, we examine the mRNA levels of pro-inflammatory cytokines and chemokines in WT and PepT1-KO mice with or without CAC induction. We found that the expression levels of IL-6, Cxcl2, IL-22 and Tnf-α were significantly increased in WT mice after AOM/DSS treatment. Importantly, while IL-6 and Cxcl-2 where only moderately elevated in AOM/DSS-treated PepT1-KO mice, IL-22 and Tnf-α where significantly elevated (FIG. 3G). The expression level of IL-10 in PepT1-KO mice tended to be lower than that in WT mice, but no significant difference was observed regardless of the genotype or treatment (FIG. 3G). Overall, these results indicate that AOM/DSS-associated intestinal inflammation was attenuated in PepT1-KO mice compared to WT mice. Taken together, these data indicate that PepT1-KO mice are protected against AOM/DSS-induced tumorigenesis through a partial inhibition of tumorigenic intestinal inflammation. This supports our hypothesis that PepT1 plays a central role in the initiation/exacerbation of CAC in mice.

Figure 4:
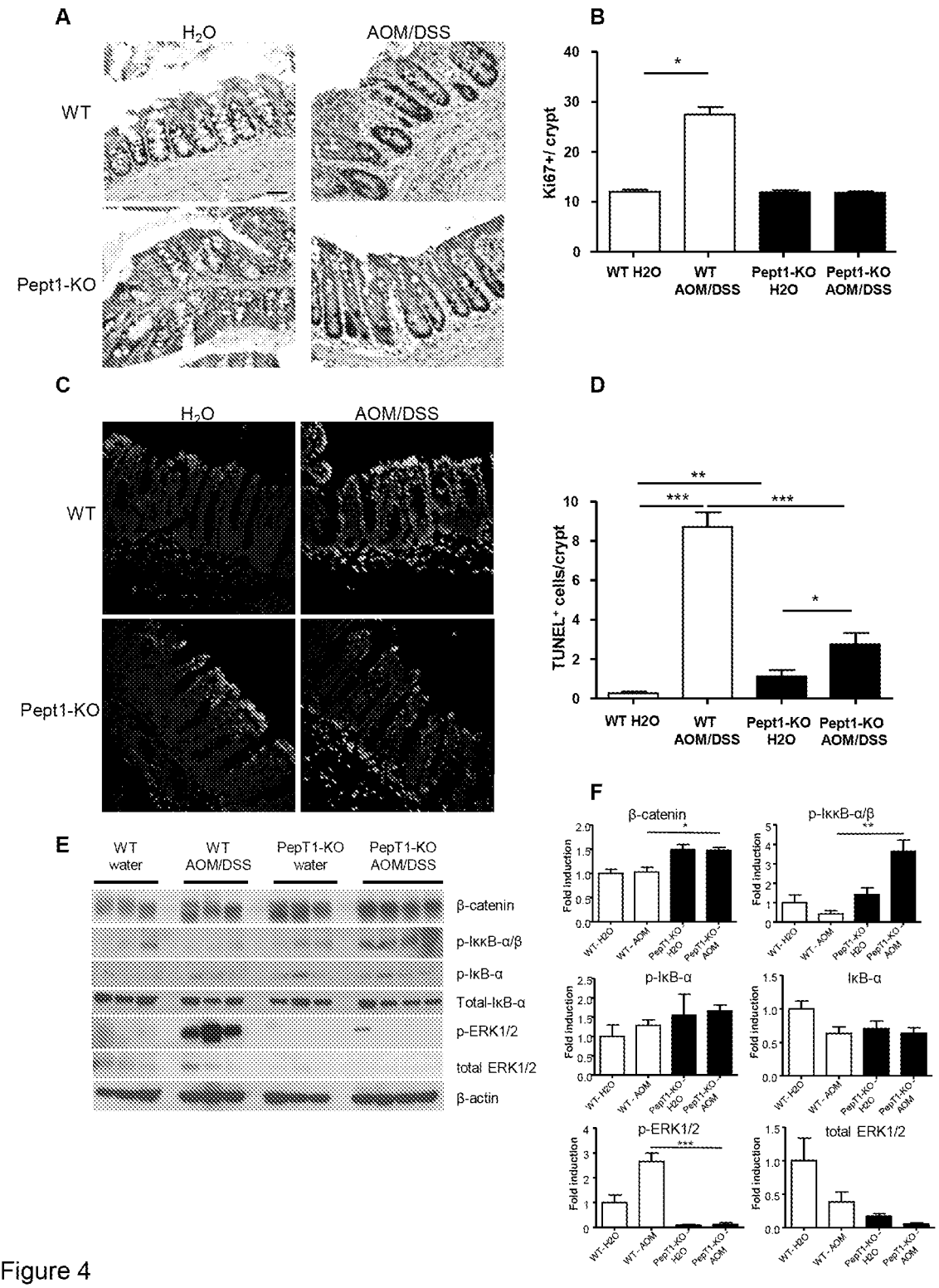
FIGS. 4A-4F are a collection of data illustrating that PepT1 knockout decreases colonic epithelial proliferation, modifies epithelial apoptosis and inhibits tumorigenesis-related signaling.

PepT1-KO mice elicit a beneficial balance of proliferation and apoptosis in the colonic mucosa associated with inhibition of tumorigenesis-related signaling: Ki67 staining demonstrated that there was no significant difference in cellular proliferation among water-treated (control) WT and PepT1 mice as well as AOM/DSS-treated PepT1-KO mice, whereas AOM/DSS-treated WT mice had significantly more Ki67-positive cells per crypt (FIGS. 4A-B). This indicates that, in the absence of PepT1, proliferation of crypt epithelial cells is inhibited. Next, we used TUNEL staining to determine the levels of apoptosis in colonic mucosa sections from WT and PepT1-KO mice. The basal level of apoptosis was slightly but significantly higher in PepT1-KO mice compared to WT mice, and the number of apoptotic cells in the epithelia of WT mice and (to a lesser extent) PepT1-KO mice was significantly increased after AOM/DSS treatment (FIGS. 4C-4D). Thus, PepT1 deficiency appears to be protective against the proliferative and abnormal apoptosis status induced by AOM/DSS treatment. In order to investigate whether PepT1 deficiency inhibits tumorigenesis signaling pathways, accumulation of proteins involved in tumorigenesis were analyzed by Western blotting. Increased levels of phosphorylated I$\kappa\kappa$-$\alpha/\beta$ were observed in AOM/DSS-treated PepT1-KO mice compared to AOM/DSS-treated WT mice, whereas no difference was observed in the levels of phosphorylated I$\kappa$B-$\alpha$ and total I$\kappa$B-$\alpha$ between the two genotypes (FIGS. 4E-4F), suggesting that inhibition of the NF-$\kappa$B pathway is not the mechanism underlying attenuated tumor growth associated with PepT1 deficiency. $\beta$-Catenin levels were unaltered in AOM/DSS-treated WT mice and comparably treated PepT1-KO mice, whereas the levels of phosphorylated ERK1/2 were drastically increased in AOM/DSS-treated WT mice but was not altered in AOM/DSS-treated PepT1-KO mice, compared to the relevant controls (FIGS. 4E-4F). This finding suggests that PepT1 deficiency may antagonize/protect from the AOM/DSS-induced ERK pathway. Together, these results suggest that inhibition of the tumor-growth-promoting ERK pathway (Lengyel et al., *Oncogene* 14:2563-73, 1997; Rice et al., *Cancer Res.* 61:1541-1547, 2001) might be involved in the inhibition of DSS/AOM-associated tumor growth observed in PepT1-K0 mice.

Figure 5:
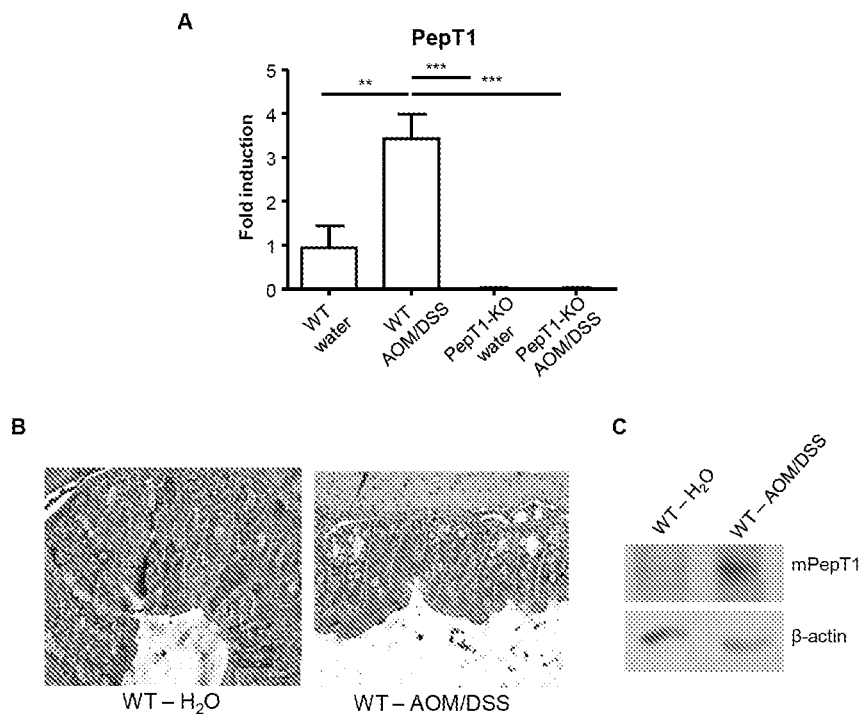
FIGS. 5A-5C are a collection of data illustrating that PepT1 expression is upregulated during colon cancer in mice.
Figure 6:
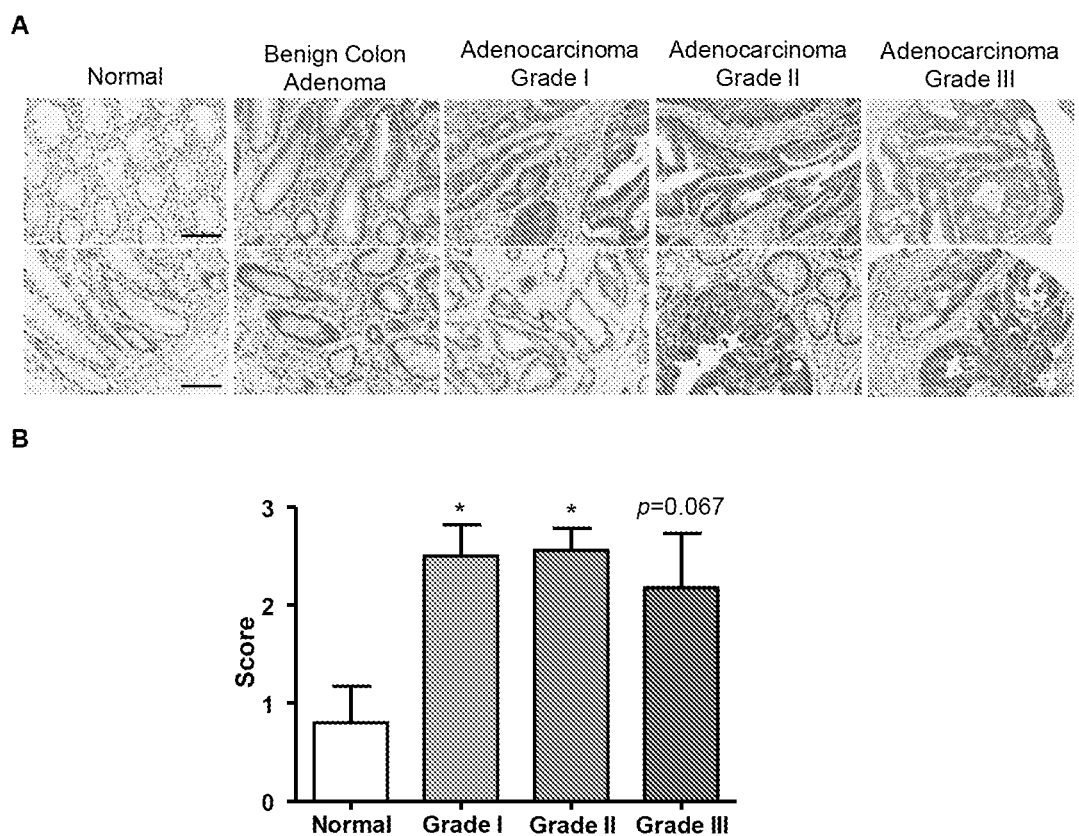
FIGS. 6A-6B are a collection of data illustrating that PepT1 expression is upregulated in colon cancer.

KPV prevents intestinal inflammation and tumorigenesis during colitis-associated carcinogenesis in a PepT1 dependent manner: The analysis of PepT1 expression at the mRNA and proteins levels both indicated that PepT1 levels were upregulated in the colons of AOM/DSS-treated WT mice (FIGS. 5A and 5C). WT mice treated with AOM/DSS had increased PepT1 staining in epithelial cells lining the colon compared to water-treated (control) mice (FIG. 5B). These immunohistochemical data were further verified by Western blot analysis of whole-colon lysates (FIG. 5C), where PepT1 expression was found increased in the colon of AOM/DSS-treated WT animals. Therefore, we predicted that colonic PepT1 would be also upregulated in colon cancer patients, as previously described for bladder cancer specimens at mRNA levels (Hagiya et al., *Photodiagnosis Photodn. Ther.* 10:288-95, 2013). To determine if PepT1 was upregulated during human disease, we analyzed a human tissue microarray, stained for hPepT1, that included paraffin-embedded samples from control patients and colon cancer patients with various stages of malignancies from Grade I to Grade III, as well as patients with benign colon tumors (male and female patients ranging in age from 19 to 92). The images were then analyzed for epithelial/tumor cells hPepT1 staining and scored. Most of the colon cancer patients demonstrated hPepT1 staining in their epithelial and/or tumor cells (FIGS. 6A-6B). In normal colon samples, some hPepT1 staining was observed in cells surrounding the epithelium, most likely immune cells (Charrier et. al., *Lab. Invest.* 86:490-503, 2006). Importantly, the majority of the colon tumor samples showed increased staining relative to both normal and benign tissues (FIG. 6B).

Figure 3:
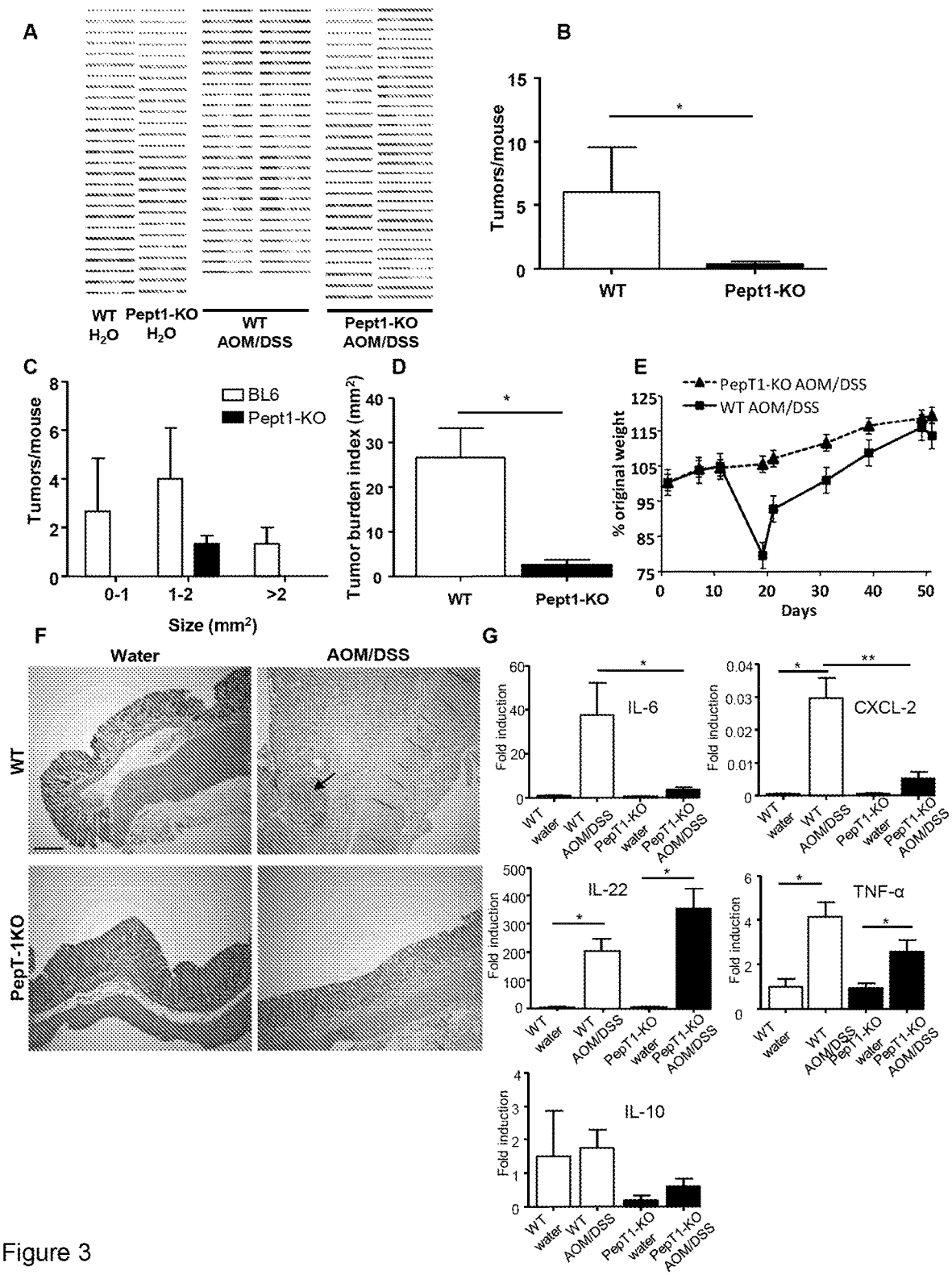
FIGS. 3A-3G are a collection of data illustrating that inflammation and tumor growth are reduced PepT1-KO mice. WT and PepT1-KO mice were IP injected with AOM (10 mg/kg body weight) and maintained for 7 days, then subjected to a two-cycle DSS treatment with each cycle consisting of 7 days of 2.5% DSS and 14 days of unmodified (DSS-free) $H_2O$.
Figure 7:
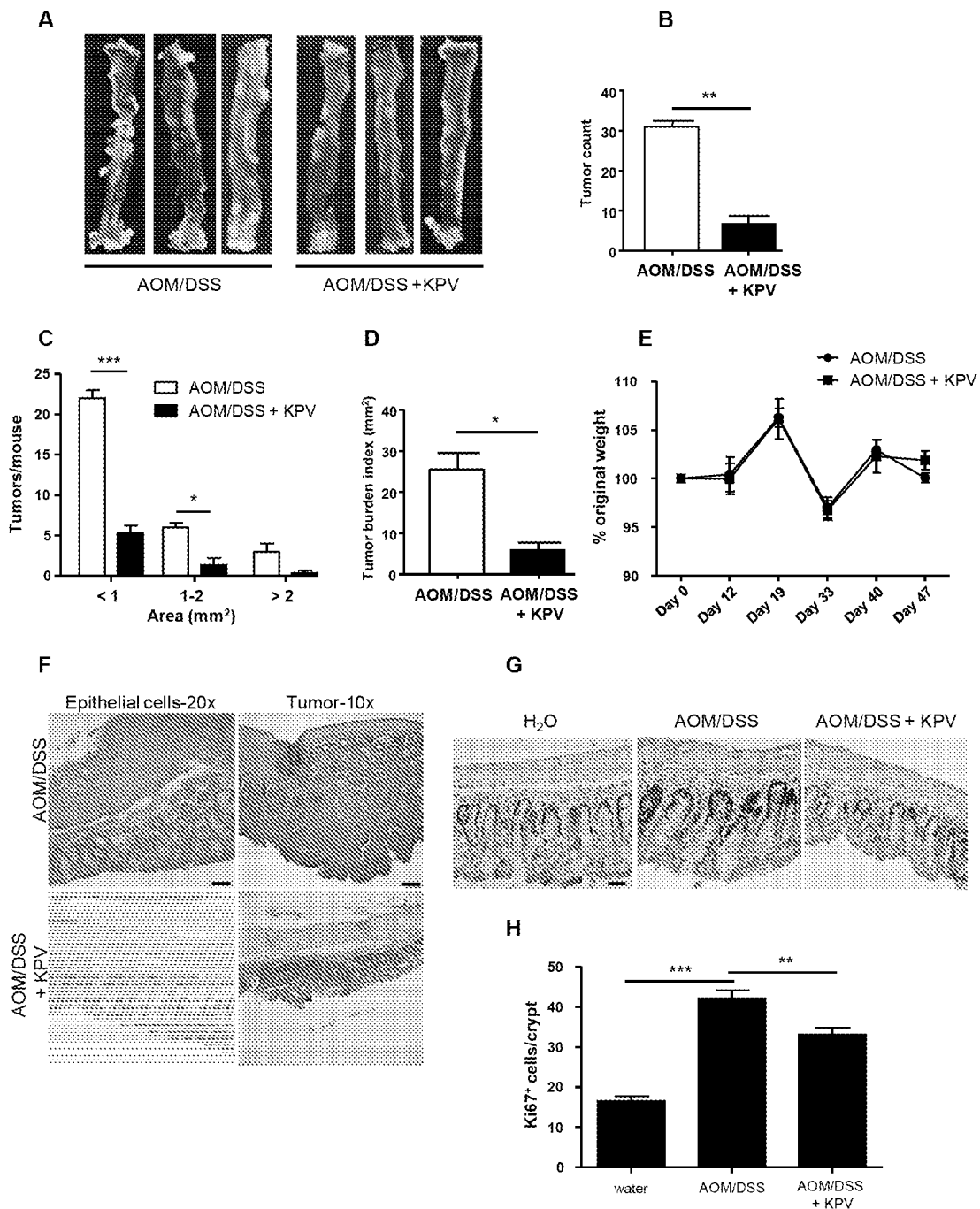
FIG. 7A-7H are a collection of data illustrating that KPV decreases inflammation and tumorigenesis during CAC. WT mice were treated with AOM followed by two cycles of DSS, during which mice were co-treated with or without 100 μM KPV.
Figure 8:
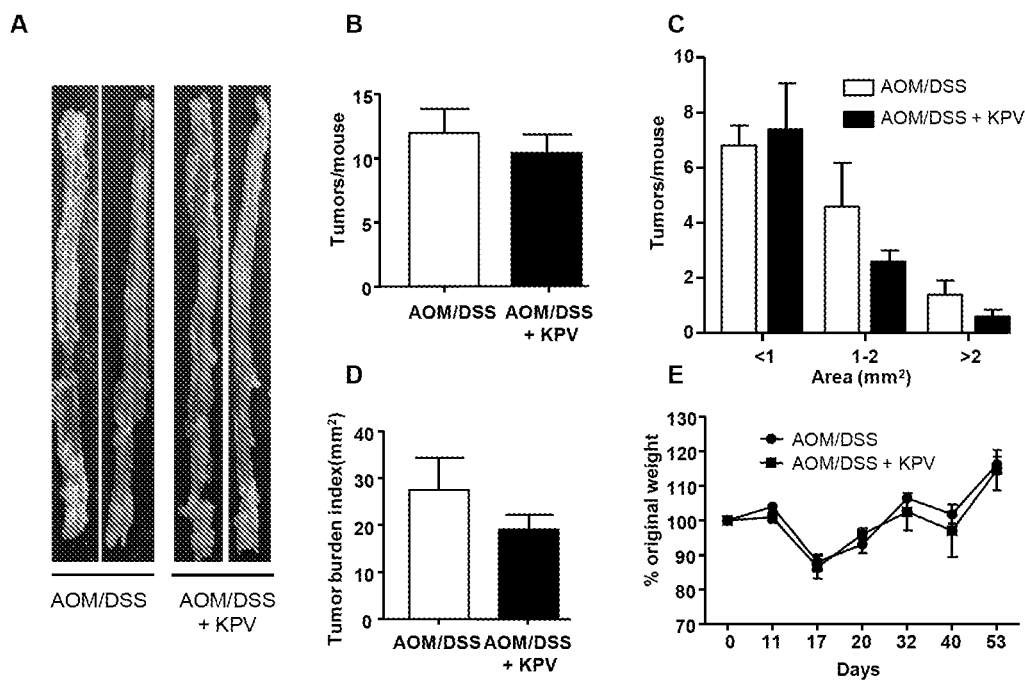
FIGS. 8A-8E are a collection of data illustrating that KPV's inhibitory effect is abrogated in PepT1-KO mice. PepT1-KO mice were treated with AOM followed by two cycles of 3% DSS, during which time a subset of the mice were co-treated with 100 KPV.

Several studies have previously shown that the KPV tri-peptide decreases inflammation and attenuates DSS-induced colitis (Dalmasso et al., *Gastroenterology,* 134:166-178, 2008; Laroui, et al., *Gastroenterology* 138:843-853 el-2, 2010; Kannengiesser et al., *Inflamm. Bowel Dis.* 14:324-331, 2008). Our laboratory has also demonstrated that KPV is transported via PepT1 in vitro in Caco-2/BBE cells (Dalmasso et al., *Gastroenterology* 134:166-178, 2008). Therefore, we hypothesized that KPV may help prevent colon tumorigenesis in the AOM/DSS-induced CAC model. To test this hypothesis, WT mice were treated with AOM/DSS or AOM/DSS+KPV (during the DSS cycles). We found that WT mice given KPV in conjunction with AOM/DSS exhibited drastic decreases in colon tumorigenesis, as revealed by tumor numbers, sizes and overall colonic tumor burdens (FIGS. 7A-D) compared to AOM/DSS-only treated animals. While both groups of mice lost similar amounts of weight during DSS treatment (FIG. 7E), KPV-treated mice exhibited decreased inflammation, fewer aberrant crypt foci, decreased cellular infiltration (as seen on H&E-stained sections), and less epithelial cell proliferation (i.e., fewer Ki67$^+$ cells/crypts) (FIGS. 7F-7H). In order to investigate any putative protective effect of KPV administration in pepT1-KO mice, the colitis-associated cancer protocol was slightly modified based on the relatively low penetrance of the disease in pepT1-deficient animals (FIG. 3). AOM concentration was increased to 15 mg/kg and DSS was increased to 3% in order to favor tumor development. We observed that, contrary to WT mice, PepT1-KO animals were not protected from tumorigenesis by KPV administration, as revealed by tumor numbers, sizes, and tumor burden that remained unchanged between the AOM/DSS and AOM/DSS+KPV groups (FIGS. 8A-8D). These data importantly revealed that KPV acts at least in part through PepT1, opening an important potential therapeutic avenue for the treatment of tumorigenesis in the colon. In the current study we have determined that overexpression of PepT1 in intestinal epithelial cells leads to increased inflammation and colonic tumor burden in a murine model of CAC, strongly suggesting that PepT1 plays a crucial role in CAC. Previous reports showed that PepT1 protein expression is upregulated in the colon under conditions of chronic inflammation such as IBD (Merlin et al., *Gastroenterology* 120:1666-1679, 2001). Upregulation of colonic PepT1 may lead to increased interactions between bacterial peptides and intracellular innate immune receptors, including NOD receptors, thus triggering downstream activation of proinflammatory signaling pathways (Dalmasso et. al., *Gastroenterology* 141:1334-45, 2011; Laroui et al., *J. Biol. Chem.* 286:31003-13, 2011). Furthermore, previous studies have shown that bacteria are required for the initiation of colonic inflammation and subsequent dysplasia and tumorigenesis (Itzkowitz and Yio, *Am. J. Physiol. Gastrointest. Liver Physiol.* 287:G7-17, 2004). Future studies are warranted to assess the role of PepT1-bacterial interactions in these processes, and whether such interactions contribute to the progression of CAC.

Our results also demonstrated that the TG mice had increased expression of proinflammatory cytokines and chemokines and decreased expression of the anti-inflammatory cytokine IL-10 compared to WT mice.

It has been reported that IL-10-deficient mice develop spontaneous colitis, and after 3 months and 6 months, 25% and 60% of the mice, respectively, develop adenocarcinoma (Berg et al., *J. Clin. Invest.* 98:1010-20, 1996). Thus, IL-10 appears to play an important role in intestinal inflammation.

In addition, colonic PepT1 protein is expressed in IL-10–/– mice that show signs of colitis, but not in non-colitic IL10–/– mice (Chen et al., *Am. J. Physiol. Gastrointest. Liver Physiol.* 299:G1287-97, 2010), suggesting that PepT1 contributes to the development of colitis in this model. In IL-10-deficient mice, tumorigenesis was decreased by the administration of exogenous IL-10, even after colitis had developed (Ullman et al., *Gastroenterology* 140:1807-16, 2011; Berg et al., *J. Clin. Invest.* 98:1010-20, 1996). Following the induction of the CAC tumor model, we herein found that PepT1-overexpressing TG mice had increased inflammation, larger tumors and greater overall tumor burdens compared to WT mice, suggesting that PepT1 expression in intestinal epithelial cells may enhance tumor cell growth or survival in the presence of a carcinogenic assault (here, AOM/DSS treatment). Interestingly, we found that the number of tumors did not vary significantly between WT and TG mice subjected to AOM/DDS treatment, suggesting that the initiation of tumorigenesis may not be affected by the expression level of PepT1 in the colon. Alternatively, PepT1 appears to enhance the proliferation and survival of tumor cells, contributing to the presence of larger tumors throughout the colon. In agreement with this hypothesis, we found that proliferation was increased in epithelial crypts from TG mice, while apoptotic cells were decreased. The tumor number was significantly lower in PepT1-KO mice than in WT mice, however, suggesting that different pathways are involved in the protective effect observed in PepT1-KO mice versus the aggravating effect observed in TG mice. To test this hypothesis, we used Western blot to examine various proteins involved in the pro-survival, proliferation and tumorigenesis signaling pathways. AOM/DSS treatment upregulated NF-κB and Wnt in TG mice compared to WT mice, but no such change was seen in PepT1-KO mice. Conversely, phosphorylated ERK1/2 was similarly upregulated following AOM/DSS treatment of TG and WT mice, but this upregulation was abrogated in PepT1-KO mice. This suggests that the absence of PepT1 inhibits the ERK pathway, potentially explaining (at least in part) the inhibition of tumor development and growth observed in PepT1-KO mice. KPV, a tripeptide from the C-terminus of α-melanocyte-stimulating hormone, mediates anti-inflammatory effects (Hiltz and Lipton, *FASEB J.* 3:2282-2284, 1989; Kelly et al., *Peptides* 27:431-7, 2006). Previous results demonstrated that KPV is a substrate for and is actively transported by PepT1 in vitro (Dalmasso et al., *Gastroenterology* 134:166-78, 2008). Following stimulation with pro-inflammatory cytokines, Caco2-BBE and Jurkat cells that were co-treated with KPV demonstrated attenuated NF-κB activation and decreased pro-inflammatory cytokine production (Dalmasso et al., *Gastroenterology* 134: 166-78, 2008). Our present data importantly demonstrate that KPV treatment is able to decrease DDS-induced intestinal inflammation and tumorigenesis. This is occurring in a PepT1-dependent manner, since PepT1-KO animals were not protected from tumorigenesis by KPV administration. IBD-related inflammation has been implicated in increasing the risk of colorectal cancer, but the existing studies have failed to show any positive link between anti-inflammatory drugs commonly used to treat IBD and a decreased risk of colon cancer (Farraye et al., *Gastroenterology* 138:746-774, 74 el-4; quiz e12-3, 2010). Therefore, when testing new therapeutic options for IBD, it may be useful to assess the efficacy and chemopreventive potential of these drugs. Overall, further studies are warranted to determine the precise mechanism by which KPV decreases tumorigenesis in this model, and to demonstrate that this tripeptide is beneficial for humans with colon cancer.

Since colonic PepT1 is expressed at minimal levels or not at all in healthy individuals, treatments that effectively downregulate PepT1 expression may attenuate inflammation and reduce the risk for tumorigenesis in IBD patients. For example, IL-10$^{-/-}$ mice were treated with the probiotic *Lactobacillus plantarum* exhibited reduced PepT1 expression and activity as well as attenuated colitis compared to vehicle-treated IL-10$^{-/-}$ animals (Chen et al., *Am. J. Physiol. Gastrointest. Liver Physiol.* 299:G1287-97, 2010).

Alternatively, treatments that exploit PepT1's transporter activity will likely increase the effectiveness of particular drugs by enhancing their bioavailability after oral administration. PepT1 has been shown to transport several types of peptide-derived drugs including antibiotics, inhibitors of angiotensin-converting enzyme, anticancer and antiviral drugs (Adibi, *Am. J. Physiol. Gastrointest. Liver Physiol.* 285: G779-88, 2003; Thwaites and Anderson, *Exp. Physiol.* 92:603-19, 2007; Adibi, *Gastroenterology* 113:332-40, 1997). Several studies have shown that the PepT1 substrate and antitumor drug, bestatin, decreases cell proliferation, ameliorates tumor growth (Nielsen and Brodin, *Current Drug Targets* 4:373-388, 2003), inhibits the growth of colon adenocarcinoma (Ayyadurai et. al., *Lab. Invest.* 93:888-99, 2013), and decreases the growth of myeloid leukemia C1498 cells in vivo (Abe et. al., Gan, 75:89-94, 1984). Finally, several studies have shown that PepT1 is expressed by cancer cells other than colorectal cancer cells (Inoue et al., *Cancer Lett.* 230:72-80, 2005; Mitsuoka et al., *Eur. J. Pharm. Sci.* 40:202-208, 2010; Gonzalez et al., *Cancer Research* 58:519-525, 1998), including gastric and pancreatic cancer cells. Therefore, the transporter activity of PepT1 may be used to address these other types of cancer. Future studies may identify other types of tumors that demonstrate increased PepT1 expression.

What is claimed is:

1. A method of treating a patient who has colorectal cancer with up-regulated intestinal $H^+$-coupled di/tripeptide transporter (PepT1) expression in colon tumors relative to normal tissue, or of reducing the likelihood that a patient will develop colorectal cancer or experience a recurrence of colorectal cancer, the method comprising administering to the patient an amount of an anti-inflammatory tri-peptide effective to reduce tumor number, tumor size, or tumor burden in the patient relative to a control subject not treated by the method, reduce the likelihood that a patient will develop colorectal cancer, or experience a recurrence of the cancer, wherein the anti-inflammatory tri-peptide is selected from the group consisting of Lys-Pro-Val (KPV), KPV stereochemical analogues, and post-translationally modified KPV at the C- and/or N-terminal, that targets PepT1, wherein the colorectal cancer has up-regulated PepT1 expression in colon tumors relative to normal tissue.

2. The method of claim 1, wherein the tri-peptide is the tri-peptide Lys-Pro-Val (KPV).

3. The method of claim 1, wherein the tri-peptide is formulated for oral administration.

4. The method of claim 1, wherein the tri-peptide is formulated for parenteral administration.

5. The method of claim 1, further comprising a step of identifying a patient in need of treatment for colorectal cancer or a patient who has an increased risk of developing colorectal cancer or experiencing a recurrence thereof.

6. The method of claim 5, wherein the method further comprises determining whether the level of PepT1 mRNA or protein is elevated in a biological sample from the patient.

7. The method of claim 1, wherein the patient has colorectal cancer and the method further comprises a radiation treatment, a surgical intervention, or administering a second chemotherapeutic agent.

8. The method of claim 1, wherein the patient has an inflammatory bowel disease (IBD) and the method further comprises administering a second agent that treats the IBD, the second agent being optionally fused or conjugated to the tri-peptide that targets the PepT1.

9. The method of claim 8, wherein the second agent is diphenoxylate, an antibiotic, bestatin, sulfasalazine, or a corticosteroid.

10. The method of claim 1, wherein the colorectal cancer is colitis-associated cancer.

11. The method of claim 1, wherein the colorectal cancer is not sporadic colorectal cancer.

12. The method of claim 1, wherein the tri-peptide affects a PepT1-dependent and nuclear factor-κB (NF-κB)-independent pathway.

* * * * *